US011216062B2

(12) United States Patent
 Cha

(10) Patent No.: US 11,216,062 B2
(45) Date of Patent: Jan. 4, 2022

(54) WEARABLE TERMINAL AND METHOD FOR OPERATING SAME

(71) Applicant: INBODY CO., LTD., Seoul (KR)

(72) Inventor: Kichul Cha, Seoul (KR)

(73) Assignee: INBODY CO., LTD., Seoul (KR)

( * ) Notice: Subject to any disclaimer, the term of this patent is extended or adjusted under 35 U.S.C. 154(b) by 0 days.

(21) Appl. No.: 16/467,692

(22) PCT Filed: Dec. 29, 2017

(86) PCT No.: PCT/KR2017/015725
§ 371 (c)(1),
(2) Date: Jun. 7, 2019

(87) PCT Pub. No.: WO2018/124809
PCT Pub. Date: Jul. 5, 2018

(65) Prior Publication Data
US 2020/0064906 A1  Feb. 27, 2020

(30) Foreign Application Priority Data

Dec. 29, 2016 (KR) .................. 10-2016-0182948
Dec. 28, 2017 (KR) .................. 10-2017-0182149

(51) Int. Cl.
*G06F 3/01* (2006.01)
*A61B 5/318* (2021.01)
(Continued)

(52) U.S. Cl.
CPC ............ *G06F 3/011* (2013.01); *A61B 5/0205* (2013.01); *A61B 5/026* (2013.01); *A61B 5/0531* (2013.01);
(Continued)

(58) Field of Classification Search
CPC ......... A61B 5/681; G06F 3/017; G06F 3/014; G06F 2200/681
See application file for complete search history.

(56) References Cited

U.S. PATENT DOCUMENTS 9,971,313 B2 * 5/2018 Chung .................. G06F 3/017
2013/0235704 A1 * 9/2013 Grinberg ................ G04G 21/08
368/69
(Continued)

FOREIGN PATENT DOCUMENTS

KR   10 20150000206 A    1/2015
KR   10 2015 0138831 A  12/2015
(Continued)

OTHER PUBLICATIONS

Chan, Marie et al., "Smart Wearable Systems: Current Status and Future Challenges", Artificial Intelligence in Medicine, pp. 137-156, vol. 56, Issue 3, Nov. 2012.

*Primary Examiner* — Sepehr Azari
(74) *Attorney, Agent, or Firm* — Boyle Fredrickson S.C.

(57) ABSTRACT

Disclosed is a wearable terminal. The terminal may comprise: a detection circuit; a first electrode and a second electrode which are connected to the detection circuit to form open loop circuits, respectively, and are spaced apart from each other; and a control unit for controlling the wearable terminal to perform a pre-configured function when the first electrode and the second electrode simultaneously come into contact with a part of a user's body, and the detection circuit, the first electrode, and the second electrode then form a signal pathway through the part of the user's body.

18 Claims, 18 Drawing Sheets

(51) Int. Cl.

| | | |
|---|---|---|
| *A61B 5/00* | (2006.01) | |
| *A61B 5/0531* | (2021.01) | |
| *A61B 5/0537* | (2021.01) | |
| *G06F 3/0346* | (2013.01) | |
| *G06F 1/16* | (2006.01) | |
| *A61B 5/0205* | (2006.01) | |
| *A61B 5/026* | (2006.01) | |
| *G06F 3/041* | (2006.01) | |
| *A61B 5/021* | (2006.01) | |
| *A61B 5/024* | (2006.01) | |

(52) U.S. Cl.
CPC .......... *A61B 5/0537* (2013.01); *A61B 5/318* (2021.01); *A61B 5/681* (2013.01); *A61B 5/6843* (2013.01); *A61B 5/748* (2013.01); *G06F 1/163* (2013.01); *G06F 3/017* (2013.01); *G06F 3/0346* (2013.01); *G06F 3/041* (2013.01); *A61B 5/021* (2013.01); *A61B 5/02438* (2013.01); *A61B 2562/0219* (2013.01); *G06F 2200/1636* (2013.01)

(56) References Cited

U.S. PATENT DOCUMENTS

| | | | | |
|---|---|---|---|---|
| 2014/0028546 A1* | 1/2014 | Jeon | .................... | G06F 3/04842 345/156 |
| 2014/0176475 A1* | 6/2014 | Myers | .................. | A61B 5/7425 345/173 |
| 2015/0019963 A1* | 1/2015 | Park | ........................ | G06F 9/453 715/708 |
| 2015/0085621 A1* | 3/2015 | Hong | ..................... | G04C 3/002 368/10 |
| 2015/0100808 A1* | 4/2015 | Deng | ..................... | G06F 3/041 713/323 |
| 2015/0157219 A1* | 6/2015 | Lee | ........................ | A61B 5/681 600/393 |
| 2015/0173686 A1* | 6/2015 | Furuta | .................... | A61B 5/681 600/301 |
| 2015/0331510 A1* | 11/2015 | Wang | .................. | G06F 3/03547 345/173 |
| 2015/0349556 A1* | 12/2015 | Mercando | ............. | H02J 7/0044 455/573 |
| 2016/0022210 A1* | 1/2016 | Nuovo | ................. | A61B 5/7445 600/301 |
| 2016/0106337 A1* | 4/2016 | Jung | ..................... | A61B 5/0537 600/547 |
| 2016/0174870 A1* | 6/2016 | Lee | ....................... | A61B 5/0537 600/547 |
| 2016/0198977 A1* | 7/2016 | Eom | ...................... | A61B 5/02416 600/384 |
| 2016/0231848 A1* | 8/2016 | Lin | ..................... | G06F 3/04166 |
| 2016/0291638 A1* | 10/2016 | Fu | .......................... | A61B 5/021 |
| 2016/0367138 A1* | 12/2016 | Kim | ................. | G01N 33/48785 |
| 2017/0000415 A1* | 1/2017 | Lapetina | .............. | A61B 5/6843 |
| 2017/0011210 A1* | 1/2017 | Cheong | .................. | G06F 21/32 |
| 2017/0100052 A1* | 4/2017 | Jung | ................... | A61B 5/0537 |
| 2017/0209053 A1* | 7/2017 | Pantelopoulos | ... | A61B 5/02125 |
| 2017/0262105 A1* | 9/2017 | Li | ............................ | G06F 3/044 |
| 2018/0120892 A1* | 5/2018 | von Badinski | .......... | A61B 5/01 |
| 2019/0059821 A1* | 2/2019 | Pekonen | ............ | A61B 5/02438 |

FOREIGN PATENT DOCUMENTS

| | | |
|---|---|---|
| KR | 10 2016 0025722 A | 3/2016 |
| KR | 10 2016 0067572 A | 6/2016 |
| KR | 20 0481546 Y1 | 10/2016 |
| KR | 10 2016 0141567 A | 12/2016 |

\* cited by examiner (a)          (b)

WEARABLE TERMINAL AND METHOD FOR OPERATING SAME

TECHNICAL FIELD

Embodiments relate to a wearable computing terminal and, more particular, to a wearable terminal capable of measuring biosignals.

BACKGROUND ART

The description provided in this section merely provides background information related to the embodiments and does not constitute the related art.

A computing device requires a device to receive an instruction from a user. A wearable terminal needs to minimize its volume and weight, and thus an area or a position for an input device of the wearable terminal are limited.

The input device includes, for example, a push button. The push button is typically positioned on a side of a main body of the wearable terminal. When viewed from a front of a wearable terminal designed for the right-handed, a push button is positioned on the right side of a main body thereof. This type of button is inconvenient to the left-handed when pushing the button. Further, the main body is formed in a bilaterally asymmetric shape due to the button.

To normally operate the button positioned on the side of the main body without a singer slipping, the main body should be supported with another finger on the opposite side of the button. When the supporting finger is not in alignment with a direction of force of the finger pushing the button, a torque occurs, and the main body rotates.

Meanwhile, a user may operate the wearable terminal by pushing the button unintentionally during a daily life or a sporting activity. With an increase in the number of button pushes, mechanical failure may occur. There is a difficulty in implementing a waterproof function in view of a trajectory of the button which is pushed and returned.

SUMMARY OF THE INVENTION

Technical Solutions

According to an aspect, there is provided a wearable terminal with a terminal main body and a band connected to the terminal main body so as to be wearable on a body part including a wrist. The terminal may include a detection circuit, a first electrode and a second electrode which are connected to the detection circuit, and a control unit for controlling the wearable terminal to perform a pre-configured function when a part of a user's body comes into contact with the first electrode and the second electrode simultaneously, and the detection circuit, the first electrode, and the second electrode then form a signal pathway through the user's body.

When the signal pathway is formed in a sleep mode, the control unit may compare a duration of a state in which the signal pathway is formed to a preset threshold, and switch the wearable terminal from the sleep mode to an awake mode when the duration is greater than the preset threshold.

The wearable terminal may further include a sensor for sensing a contact of the user. In this example, the control unit may sense a contact gesture of the user based on whether a closed loop circuit is formed or sensing data output from the sensor, and sequentially change functions to be performed by the wearable terminal when the contact gesture is sensed in an awake mode.

The sensor may include an acceleration sensor. In this example, the control unit may sense the contact gesture by calculating an impulse applied to the wearable terminal based on sensing data output from the acceleration sensor.

The wearable terminal may further include a storing unit for storing a plurality of functions and frequencies with which the functions are performed. In this example, the control unit may compare the frequencies with respect to the plurality of functions, and set an order of changing the functions to be performed by the wearable terminal, in a descending order of the frequencies.

The wearable terminal may further include a senor for sensing a contact of the user, and a storing unit for storing a plurality of functions and a plurality of contact gestures corresponding to the plurality of functions. In this example, the control unit may detect a contact gesture of the user using sensing data output from the sensor or a temporal pattern in which the signal pathway is formed, determine whether the contact gesture of the user matches one of the plurality of contact gestures stored in the storing unit, read a function corresponding to the matching contact gesture from the storing unit, and control the wearable terminal to perform the read function.

The control unit may detect the contact gesture of the user using an impulse at a time of contact, a contact count, a contact time, a time interval between contacts, a contact region, or a combination thereof, based on the sensing data or the temporal pattern.

The contact gesture may include at least one of a push, a tap, a slide, a touch, a turn, and a flick.

Meanwhile, the pre-configured function may be sending information including set information. For example, but not limited thereto, the sensing of the information may be beacon transmission. The beacon transmission may include, for example, Bluetooth and/or Bluetooth low energy (BLE) beacon transmission.

According to another aspect, there is provided a wearable terminal with a terminal main body and a band connected to the terminal main body so as to be wearable on a body part including a wrist. The terminal may include a biosignal measurement circuit, a first electrode and a second electrode which are connected to the biosignal measurement circuit, and are positioned on a front surface of the wearable terminal to be spaced apart from each other, a third electrode and a fourth electrode which are connected to the biosignal measurement circuit, and are positioned on a rear surface of the wearable terminal to be spaced apart from each other such that the third electrode and the fourth electrode may come into contact with a part of a user's body when the user wears the wearable terminal, and a control unit for sensing a contact of a part of the user's body with the first electrode through the fourth electrode, and controlling at least one of the first electrode through the fourth electrode to operate in a biosignal measurement mode, without a separate additional input, when a predetermined time elapses while the part of the user's body is in contact with the first electrode through the fourth electrode.

When the wearable terminal operates in the biosignal measurement mode, the first electrode and the third electrode may apply currents to the user's body, the second electrode and the fourth electrode may detect a voltage of a contact site of the body, and the control unit may calculate a bioimpedance of the user based on the detected voltage and analyze a body composition of the user based on the bioimpedance.

The control unit may determine that the part of the user's body is in contact with the first electrode through the fourth electrode by sensing that the first electrode through the fourth electrode and the biosignal measurement circuit form a closed loop circuit.

The biosignal measurement mode may include at least one of a body composition measurement mode, an electrocardiogram measurement mode, a heart rate measurement mode, a blood flow rate measurement mode, and a blood pressure measurement mode.

According to still another aspect, there is provided a wearable terminal for measuring a physiological condition of a user or a motion of the user. The terminal may include a detection circuit, a first electrode and a second electrode which are connected to the detection circuit, and a control unit for controlling the wearable terminal to perform a pre-configured function when a user's body comes into contact with the first electrode and the second electrode simultaneously.

Here, when a predetermined time elapses while the user's body is in contact with the first electrode and the second electrode simultaneously in a sleep mode, the control unit may switch the wearable terminal from the sleep mode to an awake mode.

The wearable terminal may further include a sensor for sensing a contact of the user, wherein the control unit may sense a contact gesture of the user using the first electrode, the second electrode, or the sensor, and sequentially change functions to be performed by the wearable terminal when the contact gesture is sensed in an awake mode.

The sensor may include an acceleration sensor. In this example, the control unit may sense the contact gesture by calculating an impulse applied to the wearable terminal based on sensing data output from the acceleration sensor.

The wearable terminal may further include a storing unit for storing a plurality of functions and frequencies with which the functions are performed. In this example, the control unit may compare the frequencies with respect to the plurality of functions, and set an order of changing the functions to be performed by the wearable terminal, in a descending order of the frequencies.

The wearable terminal may further include a sensor for sensing a contact of the user, and a storing unit for storing a plurality of functions and a plurality of contact gestures corresponding to the plurality of functions. In this example, the control unit may sense a contact gesture of the user using a temporal pattern in which the user's body comes into contact with the first electrode and the second electrode or sensing data output from the sensor, read a function corresponding to the sensed contact gesture from the storing unit, and control the wearable terminal to perform the read function.

The control unit may detect the contact gesture of the user using an impulse at a time of contact, a contact count, a contact time, a time interval between contacts, a contact region, or a combination thereof, based on the sensing data or the temporal pattern.

The contact gesture may include at least one of a push, a tap, a slide, a touch, a turn, and a flick.

DETAILED DESCRIPTION OF PREFERRED EMBODIMENTS

Figure 1:
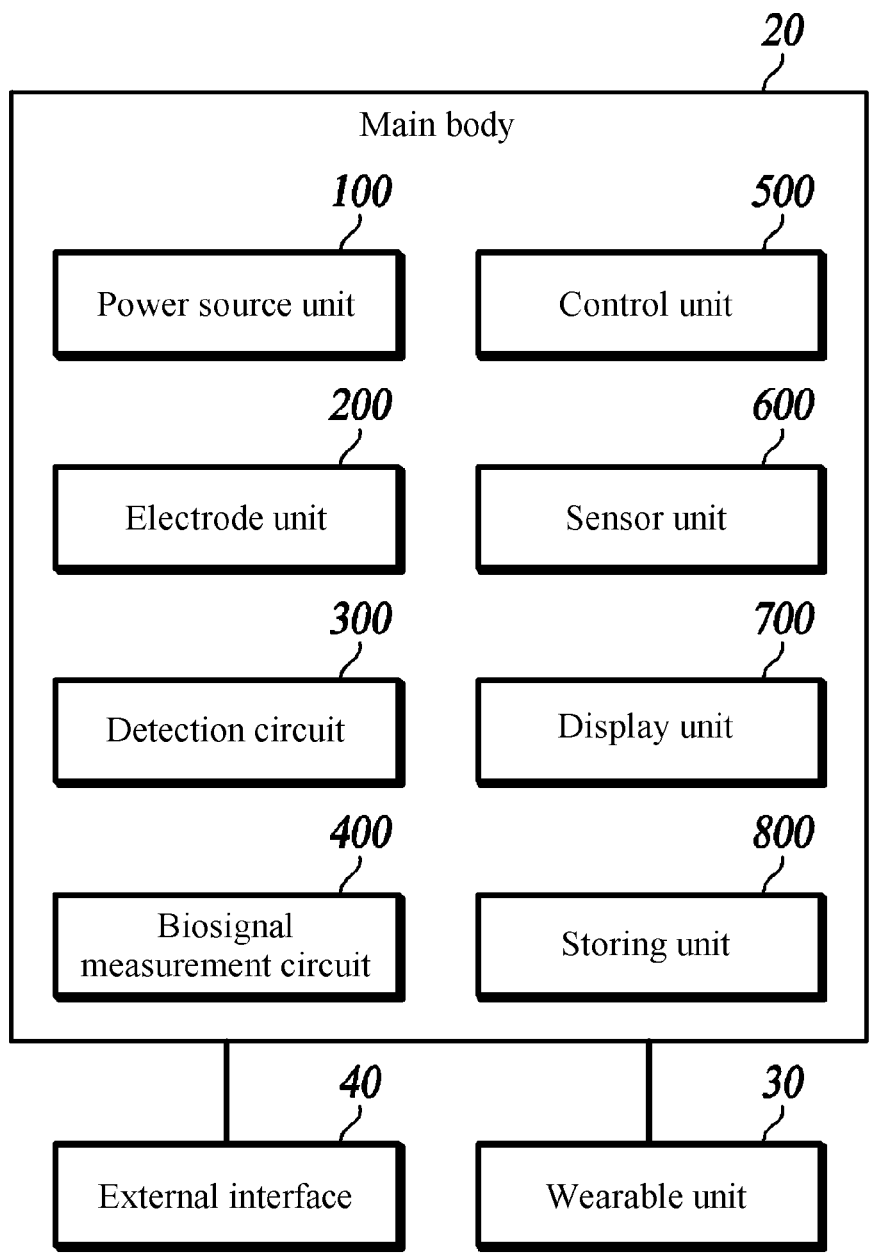
FIG. 1 is a block diagram illustrating a wearable terminal according to embodiments of the present invention.

Hereinafter, example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

Also, when a part "includes" or "comprises" an element, unless there is a particular description contrary thereto, the part can further include other elements, not excluding the other elements. In the following description, terms such as "unit" and "module" indicate a unit for processing at least one function or operation, wherein the unit and the block may be embodied as hardware or software or embodied by combining hardware and software.

In addition, terms such as first, second, A, B, (a), (b), and the like may be used herein to describe elements of the present invention. Each of these terminologies is not used to define an essence, order or sequence of a corresponding element but used merely to distinguish the corresponding element from other element(s). It should be noted that if it is described in the specification that one part "includes" or "comprises" one element, it indicates that another element may be further included and not that another element is excluded, unless described otherwise. Also, terms "-unit", "-module", etc. indicate a unit to process at least one function or operation, and may be configured through hardware or software or combination of hardware and software.

Embodiments set forth hereinafter may enable electrodes (terminals) for biosignal measurement to be used as an input interface, even with minimal buttons and/or without additionally installing physical buttons for inputs into a wearable terminal. According to some embodiments, a device may utilize electrodes used for body composition analysis as an input device of a user, rather than including a separate input device, by sensing a contact of a part of the user's body with a first electrode and a second electrode and performing a function of the device.

Meanwhile, a wearable terminal which will be described hereinafter may be, for example, but not limited to, a terminal capable of measuring biometric information such as body compositions. However, embodiments are not limited thereto. Although terminals of various shapes and purposes are not enumerated, the embodiments are not limited to a wearable terminal of a specific purpose.

FIG. 1 is a block diagram illustrating a wearable terminal according to embodiments of the present invention. As shown in FIG. 1, a wearable terminal 10 includes a main body 20 and a wearable unit 30. The main body 20 of the wearable terminal 10 wholly or partially includes a power source unit 100, an electrode unit 200, a detection circuit 300, a body composition measurement circuit 400, a control unit 500, a sensor unit 600, a display unit 700, and a storing unit 800. The main body 20 may include an external interface 40. The main body 20 and the wearable unit 30 are connected to each other and thus, have a structure to be worn by a user. The wearable terminal 10 may omit a portion of the various elements exemplarily illustrated in FIG. 1, or further include other elements.

The power source unit 100 supplies power to the elements included in the wearable terminal 10. The power source unit 100 may include a primary battery or a secondary battery. If the power source unit 100 includes a secondary battery, the external interface 40 may be a charging terminal, and the battery is charged by an external charger connected through the external interface 40. Further, the power source unit 100 may also include a wireless power receiver in addition to the battery, and the battery may be charged by receiving wireless power from a wireless power transmitter.

The electrode unit 200 is formed on an outer portion of the main body 20 so as to be contacted from an outside. The electrode unit 200 includes a plurality of electrodes, and the electrodes are disposed to be spaced apart from each other. The plurality of electrodes includes a current electrode for applying a current and a voltage electrode for detecting a voltage to measure a bioimpedance. Here, the current electrode and the voltage electrode are determined at random in a process of detecting biometric information of the user, and a role of an electrode disposed at a predetermined position is not limited to a role as a current electrode or a voltage electrode. The electrodes of the electrode unit 200 may be used in common to sense a contact of the user's body or to measure a bioimpedance, and may be connected in parallel to the detection circuit 300 for sensing a contact of the body and the biosignal measurement circuit 400 for measuring a bioimpedance.

The detection circuit 300 is a circuit for sensing a contact of the user's body, and is connected to the power source unit 100 and supplied with power therefrom. At least two electrodes of the electrode unit 200 are connected to the detection circuit 300 and form an open loop circuit therewith. In detail, the electrode unit 200 is formed on the outer portion of the main body 20, and the detection circuit 300 is formed on an inner portion of the main body, which corresponds to a form of being connected to the detection circuit 300 between an electrode and an electrode. When a part of a user's body comes into contact with the at least two electrodes connected to the detection circuit 300 simultaneously, the electrodes are connected through the user's body and form a closed loop circuit.

According to an embodiment, the detection circuit 300 may sense a change in pressure applied to the main body 20 using a touch sensor of the sensor unit 600, which will be described layer. For example, the detection circuit 300 may sense a tap such as a finger touch of the user who is wearing the wearable terminal 10.

According to an embodiment, the detection circuit 300 may sense a change in impedance outside of the wearable terminal 10 in response to a contact of the user's body. For example, the user may perform a finger touch with respect to one of the at least two electrodes included in the electrode unit 200. In this example, in response to the finger touch of the user, the detection circuit 300 may detect an overshoot peak value. The overshoot peak value occurs when a signal pathway of the open loop circuit temporarily changes in response to a contact of a finger of the user with one electrode. Further, the detection circuit 300 may sense one of a forward touch (first electrode touch) or a backward touch (second electrode touch) of the user based on a sign of the overshoot peak value.

The biosignal measurement circuit 400 is a circuit for measuring a bioimpedance of the user, and is connected to the plurality of electrodes of the electrode unit 200. The electrodes connected to the biosignal measurement circuit 400 may be divided into a current electrode and a voltage electrode. When the wearable terminal 10 operates in a bioimpedance measurement mode, the biosignal measurement circuit 400 measures the bioimpedance by applying a current to the user's body through the current electrode, and detecting a voltage through the voltage electrode.

The control unit 500 performs various functions and processes data for the wearable terminal 10 by executing a variety of software or instruction sets. For example, the control unit 500 may control functions to be performed by the wearable terminal 10 or the display unit 700 by sensing that a circuit including the detection circuit 300 and the electrodes is formed. Further, the control unit 500 may determine a motion or a physiological condition of the user by obtaining data from the biosignal measurement circuit 400, the sensor unit 600, or the storing unit 800. The control unit 500 may be implemented by a microprocessor.

The sensor unit 600 includes a plurality of sensors for measuring a motion of the user or a physiological condition of the user. The sensor unit 600 wholly or partially includes various sensors such as a touch sensor, an acceleration sensor, a gyro sensor, a proximity sensor, a red, green, and blue (RGB) sensor, an illuminance sensor, a global positioning system (GPS) sensor, a geomagnetic sensor, and an electromyogram (EMG) sensor. The touch sensor recognizes a press or a touch using a pressure or a capacitance when the user presses or touches the display unit 700 of the wearable terminal 10. The acceleration sensor senses a motion per unit time of the wearable terminal 10 by measuring an acceleration or an oscillation of an object. The gyro sensor measures a tilt of the wearable terminal 10 by sensing an orientation of the wearable terminal 10 with three spatial axes. The proximity sensor shows whether there is an object near or approaching the wearable terminal 10 using a force of an electromagnetic field without a physical contact. The RGB sensor senses a hue or a color density of light around the wearable terminal 10. The illuminance sensor senses a brightness of light around the wearable terminal 10. The GPS sensor shows a current position of the wearable terminal 10 by calculating time differences from a plurality of GPS satellites revolving around the earth. The geomagnetic sensor shows a surface azimuth angle by sensing a magnetic field of the earth. The geomagnetic sensor may be used to implement a position based service by being combined with the GPS sensor. The EMG sensor measures a degree of muscle contraction or relaxation.

The wearable terminal 10 provides information related to the wearable terminal 10 using visual, auditory, and tactile effects.

The display unit 700 provides visual information to the user. The display unit 700 may be implemented as various display panels, such as for example, a liquid crystal display (LCD), an organic light emitting diode (OLED), and a thin film transistor liquid crystal display (TFT-LCD), but are not limited thereto.

The display unit 700 may be implemented as a touch screen. The touch screen is a contact-type display configured to execute an instruction matching a predetermined portion of a screen when the user touches the predetermined portion with a hand or a special device. The touch screen may detect at least one touch point thereon based on a predetermined phenomenon which may be measured in a capacitive, resistive, optical, acoustical, inductive, mechanical, or chemical manner.

The wearable terminal 10 may further include a light for providing visual information, an oscillating unit for providing tactile information, and a speaker for providing auditory information. The light is a luminous body and may include a light emitting diode (LED), but is not limited thereto. The light provides the information by changing a color or flashing. The oscillating unit oscillates the wearable terminal 10 by regularly or irregularly rotating an eccentric mass positioned in the wearable terminal 10. The speaker converts an electrical signal into a sound wave.

The storing unit 800 stores software, instruction sets, and data for operating the wearable terminal 10. The storing unit 800 is connected to the control unit 500. The storing unit 800 may be implemented as a random access memory (RAM), a magnetic disc, a flash memory, a static random access memory (SRAM), a read only memory (ROM), an electrically erasable programmable read only memory (EEPROM), or a programmable read only memory (PROM), but is not limited thereto.

The wearable terminal 10 may further include a communication unit (not shown). The communication unit converts an electrical signal into an electromagnetic wave or converts an electromagnetic wave into an electrical signal, and performs a function of communicating with a communication network or a wearable terminal device (wherein, however, examples are not limited to the "wearable terminal device" and may include a non-wearable computing device) of another user using the electromagnetic wave. The communication unit is connected to the control unit 500. The communication unit may use various communication protocols required for wireless communication or mobile communication. The communication protocols include, for example, near field communication (NFC), ZigBee, Bluetooth, Wi-Fi, WiMAX, global system for mobile communication (GSM), third generation (3G) mobile communication, and long term evolution (LTE), but are not limited thereto.

The wearable terminal 10 transmits and receives data to and from a mobile device using the communication unit. That is, the wearable terminal 10 may be paired with an application run on the mobile device. The mobile device includes a smart phone, a tablet PC, a personal digital assistant (PDA), and a laptop computer, but is not limited thereto.

The external interface 40 performs a function of connecting the wearable terminal 10 to an external device. The external interface 40 includes an audio connection unit and a port connection unit. The audio connection unit is used for wired connection with an external audio device. For example, the audio device includes earphones and headphones. The port connection unit is used for wired connection with another computing device. The port connection unit may be implemented as a universal serial bus (USB), or another wired port.

The wearable unit 30 is formed in a structure wearable on a body. The wearable unit 30 may be detachable from the main body 20. The wearable unit 30 may be in a shape of a band, and may be implemented by a female band and a male band. The female band and the male band have width, length, and thickness suitable for being worn on any part of a human body, for example, a wrist, a forearm, an ankle, or a leg. The wearable unit 30 may be formed of synthetic resin or silicone, but is not limited thereto, and may be formed of any material which is flexible and easily bent and has a high tensile strength. The wearable unit 30 may be formed of a material little irritant to human skin.

The wearable terminal 10 may further include at least one of a heart rate measuring unit, a step count measuring unit, a walking time measuring unit, a calorie consumption calculating unit, a traveled distance measuring unit, and a battery level measuring unit.

Each of the elements of the main body 20 of the wearable terminal 10 may perform functions of the other elements together, as necessary. The elements may be implemented as a logical circuit by hardware, firmware, software, or a combination thereof. Those elements perform communication through at least one communication bus or signal line.

Figure 2A:
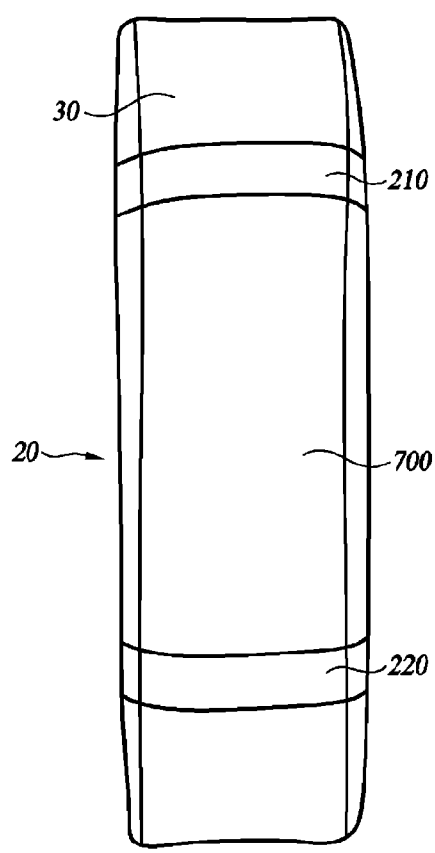
FIGS. 2A and 2B are front views illustrating a wearable terminal.
Figure 2B:
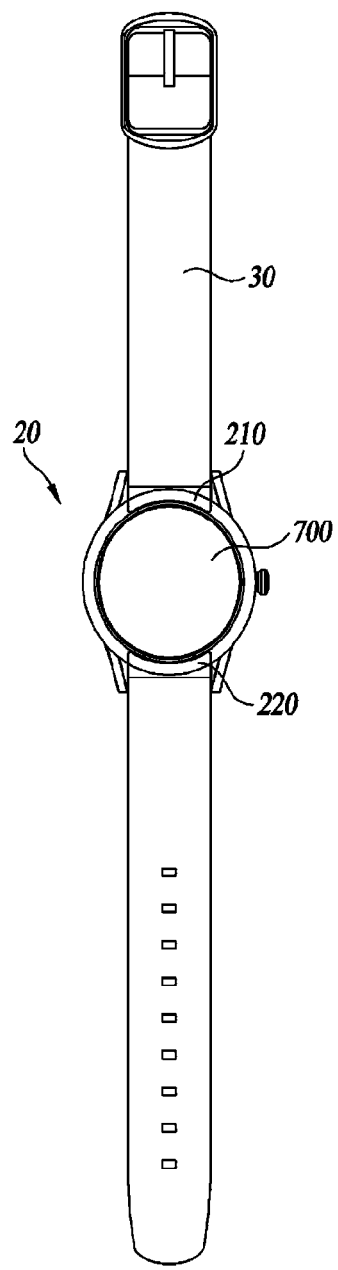

FIG. 2A is a front view illustrating a band-shaped wearable terminal, and FIG. 2B is a front view illustrating a watch-shaped wearable terminal.

Figure 3A:
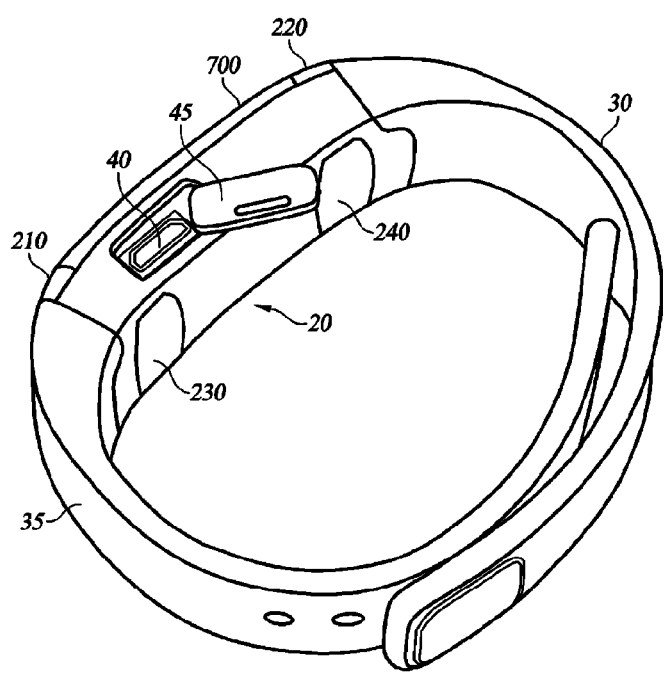
FIGS. 3A and 3B are side views illustrating a wearable terminal.
Figure 3B:
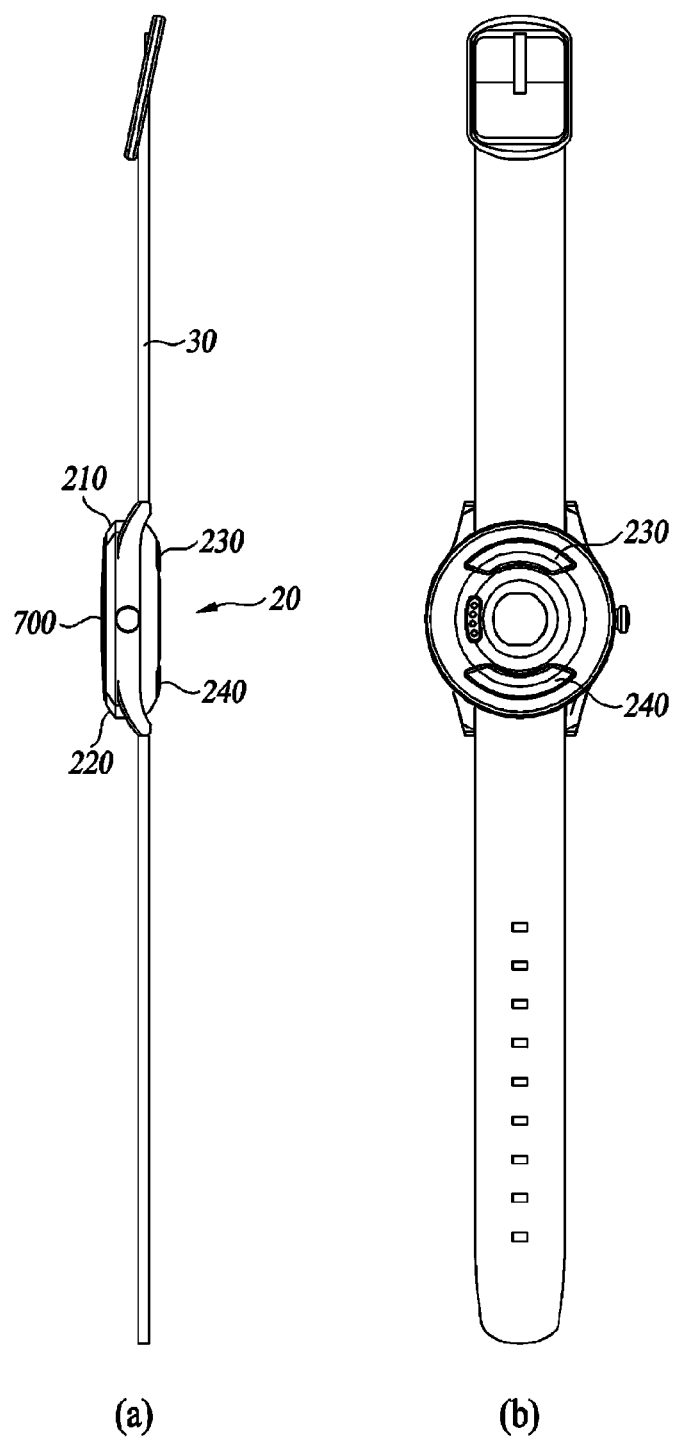

FIG. 3A is a side view illustrating the band-shaped wearable terminal, and FIG. 3B shows a side view (a) and a rear view (b) of the watch-shaped wearable terminal.

Referring to FIGS. 2A, 2B, 3A, and 3B, the wearable terminal 10 may include two wearable units 30 and 35 on both sides of the main body such that the main body 20 and the wearable unit 30 are connected and thus, have a structure to be worn by a user. The number of electrodes and positions of the electrodes may vary, as necessary. The external interface 40 may include an external interface unit cover 45 for protection from an outside.

In the configuration of the main body 20, the electrode unit 200 is formed on the outer portion of the main body 20, and may include a first electrode 210, a second electrode 220, a third electrode 230, and a fourth electrode 240.

The first electrode 210 and the second electrode 220 are formed to be out of contact with at least a part of a body when the user wears the wearable terminal 10. For example, the first electrode 210 and the second electrode 220 are positioned on a front surface of the main body 20.

Referring to FIGS. 2A, 2B, 3A, and 3B again, the third electrode 230 and the fourth electrode 240 are formed to be in contact with a part of the body when the user wears the wearable terminal 10. For example, the third electrode 230 and the fourth electrode 240 are positioned on a rear surface of the main body 20.

Figure 4A:
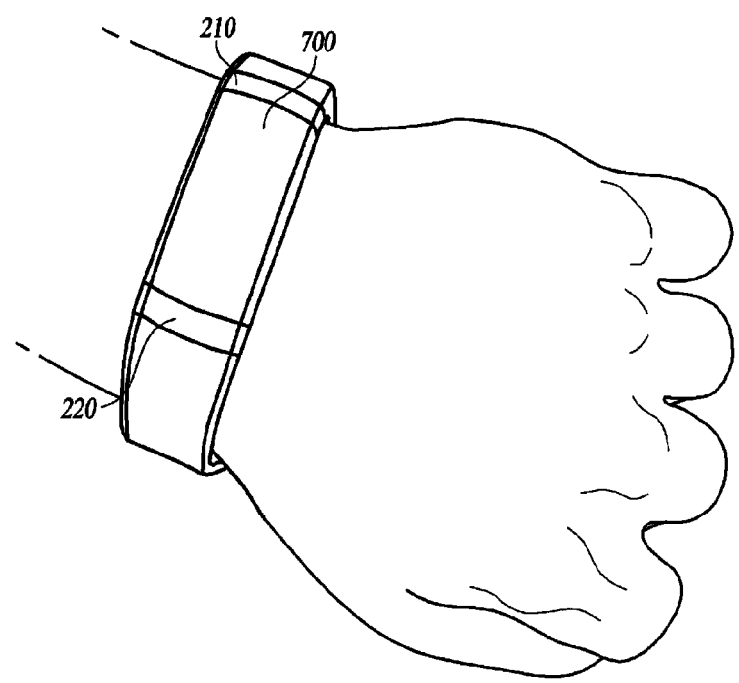
FIGS. 4A and 4B illustrate examples of a wearable terminal worn on a body.
Figure 4B:
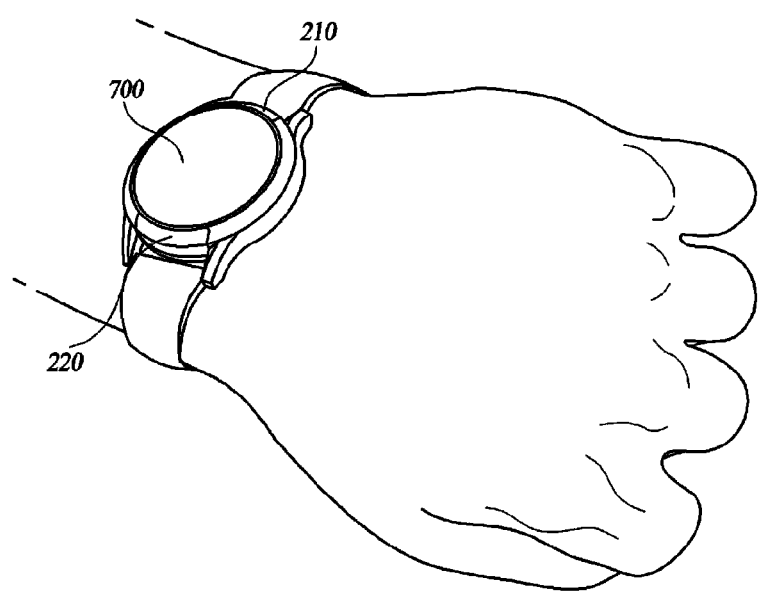

FIG. 4A illustrates a band-shaped wearable terminal worn on a body, and FIG. 4B illustrates a watch-shaped wearable terminal worn on a body. Referring to FIGS. 4A and 4B, when the wearable terminal 10 is worn on a wrist, the third electrode 230 and the fourth electrode 240 positioned on the rear surface of the main body 20 are in contact with the wrist. Referring to FIGS. 4A and 4B, when the wearable terminal 10 is worn on the wrist, the first electrode 210 and the second electrode 220 positioned on the front surface of the main body 20 are exposed to an outside and out of contact with any part of the body.

Figure 5A:
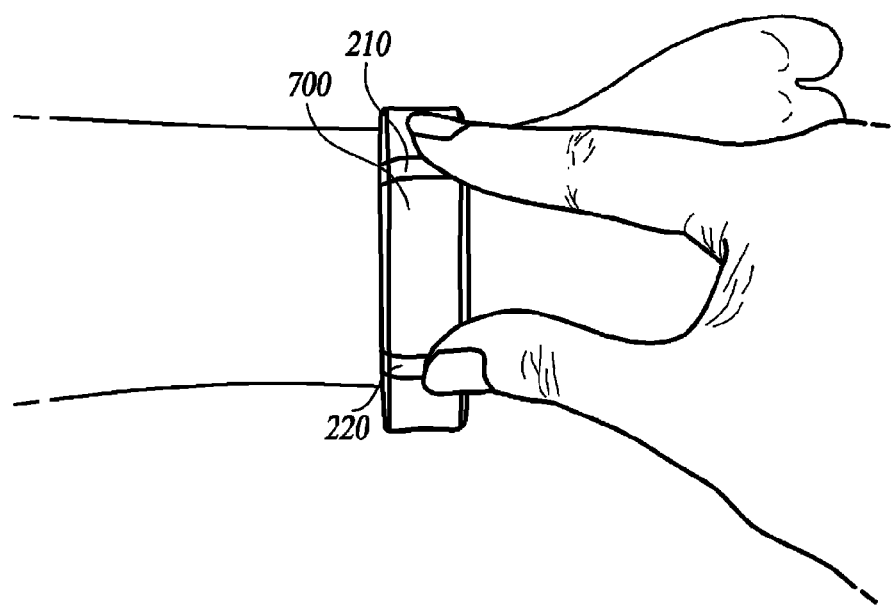
FIGS. 5A through 5D illustrate examples of a body part in contact with an electrode unit of a wearable terminal.
Figure 5B:
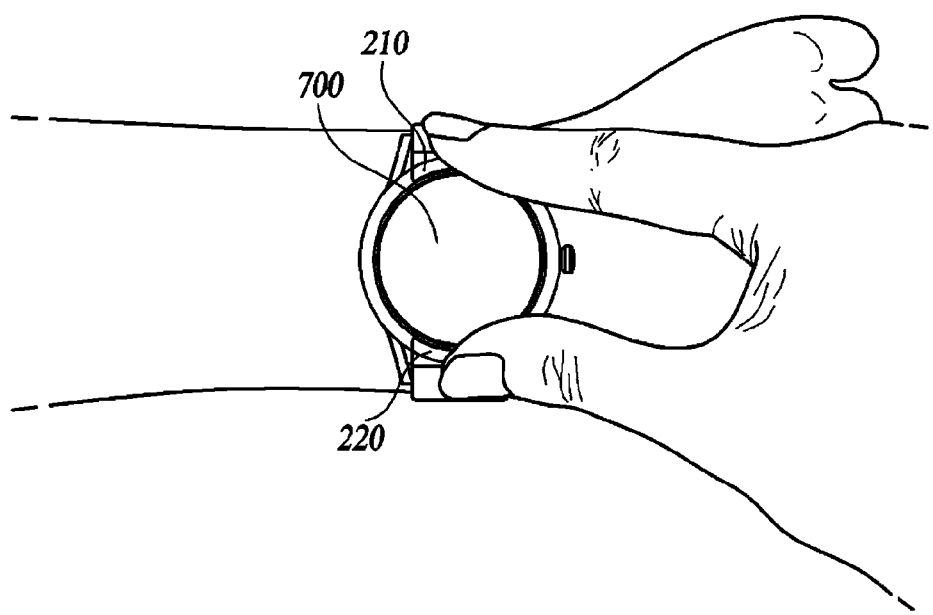
Figure 5C:
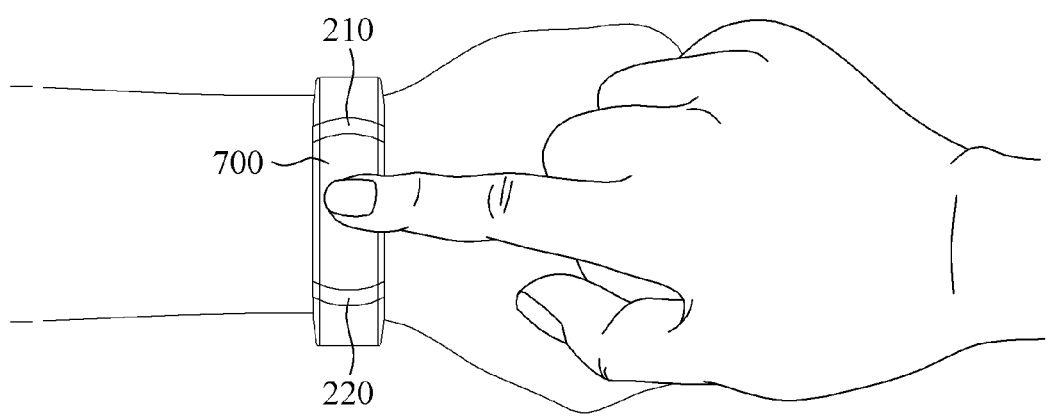
Figure 5D:
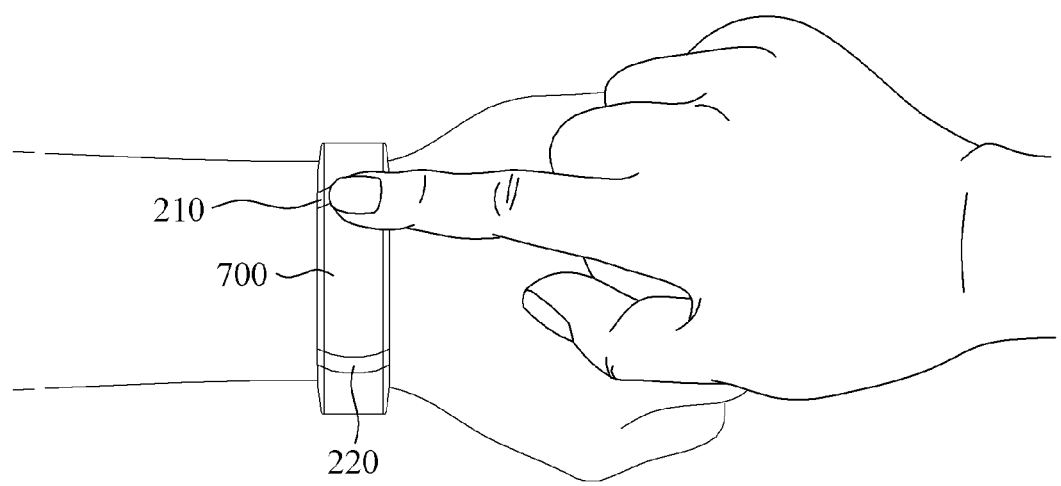

FIG. 5A illustrates an example of a body part in contact with an electrode unit of a band-shaped wearable terminal, and FIG. 5B illustrates an example of a body part in contact with an electrode unit of a watch-shaped wearable terminal. FIG. 5C illustrates an example of performing a tap with respect to a display unit of the band-shaped wearable terminal, and FIG. 5D illustrates an example of performing a forward touch on an electrode unit of the band-shaped wearable terminal. Although the example of FIG. 5D shows a process of implementing a forward touch in response to a finger of a user coming into contact with the first electrode 210, it is obvious to those skilled in the art that a backward touch may also be implemented in response to the finger of the user coming into contact with the second electrode 220.

Figure 6:
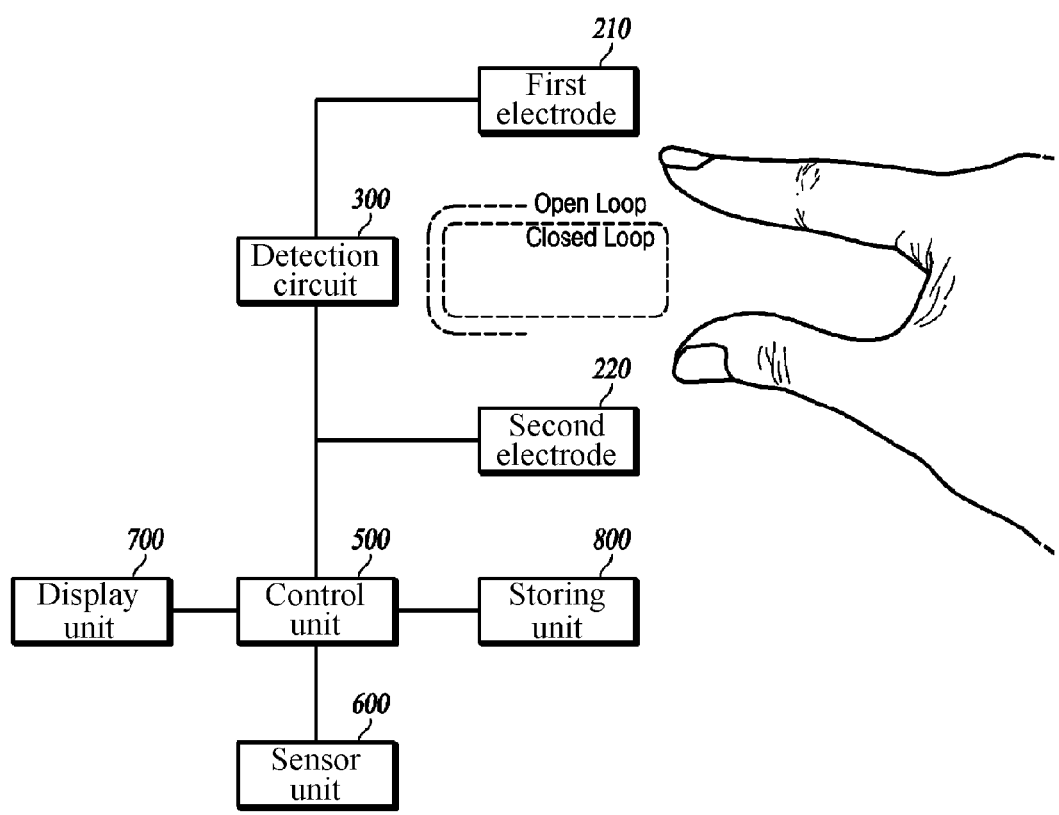
FIG. 6 is a block diagram illustrating a wearable terminal according to an embodiment of the present invention.

FIG. 6 is a block diagram illustrating a wearable terminal according to an embodiment of the present invention. Referring to FIG. 6, the first electrode 210 and the second electrode 220 are connected to the detection circuit 300 formed inside of the main body 20. In detail, as shown in FIG. 6, the detection circuit 300 is connected between the first electrode 210 and the second electrode 220, whereby an open loop circuit is formed. As in FIGS. 5A and 5B, when two fingers of a hand on which a device is not worn by a user are in contact with the electrodes 210 and 220, the first electrode 210 and the second electrode 220 are connected through the fingers of the user and form a closed loop circuit with the detection circuit 300, as shown in FIG. 6. The control unit 500 detects a contact of the user's body by sensing that the closed loop circuit is formed, and controls the wearable terminal 10 to perform a pre-configured function corresponding to the contact of the user's body.

The first electrode 210, the second electrode 220, the third electrode 230, and the fourth electrode 240 are connected to the biosignal measurement circuit 400 formed inside of the main body 20.

When the wearable terminal operates in a biosignal measurement mode, the first electrode 210 and the second electrode 220 formed on the front surface of the main body 20 correspond to a current electrode and a voltage electrode as a pair, and the third electrode 230 and the fourth electrode 240 formed on the rear surface of the main body 20 correspond to a current electrode and a voltage electrode as a pair.

In a body composition measurement mode, the biosignal measurement circuit 400 applies currents to the current electrodes and detects voltages from the voltage electrodes to measure a bioimpedance, based on a control of the control unit 500. The control unit 500 calculates a bioimpedance of the user based on the detected voltages, and analyzes a body composition of the user based on the bioimpedance. In this example, the arrangement of the current electrodes and the voltage electrodes is not fixed, and the roles of the electrodes may change depending on a design for the accuracy of body composition measurement. Further, the part of the user's body in contact with the electrodes 210 and 220 on the front surface of the main body 20 is not limited to two fingers as shown in FIGS. 5A and 5B. If an adjacent body part comes into contact with the two electrodes 210 and 220 simultaneously so as to be out of contact with the part (wrist) on which the wearable terminal 10 is worn, such as a single finger, a palm, or a back of hand, the bioimpedance may be measured.

When a body composition analysis function of the wearable terminal 10 is performed, a measurement is performed for a preset time. To calculate a more accurate body composition analysis result value, the user should be careful about two behaviors. When a bioimpedance measuring unit measures an impedance, the user should be careful not to touch one hand with the other hand. Further, while the bioimpedance measuring unit measures the impedance, the user should maintain a posture. When the measurement is completed, the bioimpedance measuring unit calculates a muscle mass, a body fat mass, a body fat percentage, and a body mass index based on an input weight. The weight may be received from a paired mobile device. When the measurement is completed, the display unit 700 displays the body fat percentage. A communication unit transmits the calculated muscle mass, the calculated body fat mass, the calculated body fat percentage, and the calculated body mass index to the paired mobile device. The communication unit transmits at least one of measured body current, voltage, and impedance to the paired mobile device.

Further, the control unit 500 senses a contact of the part of the user's body with the first electrode 210, the second electrode 220, the third electrode 230, and the fourth electrode 240, and controls the wearable terminal 10 to operate in a biosignal measurement mode, without a separate additional input, when a predetermined time elapses while the user's body is in contact with all the electrodes 210, 220, 230, and 240.

In the embodiment, the first electrode 210, the second electrode 220, the third electrode 230, and the fourth electrode 240 are separately connected to the biosignal measurement circuit 400, and the third electrode 230 and the fourth electrode 240 are in contact with the wrist of the user when the user wears the wearable terminal 10. In this example, when the user touches the first electrode 210 and the second electrode 220 with another body part, the user's body, the electrodes 210, 220, 230, and 240, and the biosignal measurement circuit 400 form a closed loop circuit. The control unit 500 determines whether the user's body is in contact with all the electrodes 210, 220, 230, and 240 by sensing that the closed loop circuit is formed, and controls the wearable terminal 10 to operate in a biosignal measurement mode.

The biosignal measurement mode may be a body composition measurement mode, an electrocardiogram measurement mode, a heart rate measurement mode, a blood flow rate measurement mode, or a blood pressure measurement mode. The control unit 500 controls the wearable terminal 10 to enter the preset biosignal measurement mode, irrespective of whether the terminal is in an awake mode or a sleep mode, when a predetermined time elapses while the part of the user's body is in contact with all the electrodes 210, 220, 230, and 240.

The wearable terminal 10 may control a device using a body part. That is, the part of the user's body may act as a switch which controls the wearable terminal 10. For example, the wearable terminal 10 may include the electrode unit 200 to control an on/off of the device, a function to be performed by the device, an operating mode of the device, and a function of transmitting beacon information from the device to a designated external device when the part of the user's body comes into contact with the electrodes.

The wearable terminal 10 operates in an awake mode. Here, the awake mode is a mode opposite to a sleep mode in which a power source unit of the wearable terminal 10 restricts operations of the units of the wearable terminal 10 or operates the units with low power to efficiently use power. That is, in the awake mode, the wearable terminal 10 performs at least one of a plurality of performable functions.

The plurality of functions may include a function of changing a function to be performed by the terminal, a function of displaying a clock, a function of analyzing a body composition, a function of displaying a heart rate, a function of displaying a step count, a function of displaying a walking time, a function of displaying a calorie consumption, a function of displaying a traveled distance, and a function of displaying a battery level.

The control unit 500 of the wearable terminal 10 may switch a mode between a sleep mode and an awake mode. When it is sensed that a closed loop circuit is formed while the wearable terminal 10 is in a sleep mode, the control unit 500 compares a duration of a state in which the closed loop circuit is formed to a preset threshold. In this example, the preset threshold is a time value for which the user should keep a body part in contact with the first electrode 210 and the second electrode 220 to enter the awake mode, and may be a time value of 1 to 2 seconds. When a duration is identical to or greater than the preset threshold as a result of comparing the duration and the preset threshold (the threshold time for entering the awake mode), the control unit 500 switches the wearable terminal from the sleep mode to the awake mode.

That is, when the wearable terminal 10 is in the sleep mode, and a predetermined time elapses while the user contacts the first electrode 210 and the second electrode 220 with a finger, the wearable terminal 10 enters the awake mode and performs one of the plurality of functions, the display unit 700 is turned on, and a screen corresponding to the function performed by the wearable terminal 10 is displayed. Similarly, based on a duration during which the state in which the closed loop circuit is formed is continued in the awake mode, the mode may be switched from the awake mode to the sleep mode. The mode may be switched from the awake mode to the sleep mode based on a time during which a contact of the user is not detected in the awake mode.

Referring to FIG. 6, a wearable terminal includes the power source unit 100, the electrode unit 200, and the control unit 500. The electrode unit 200 includes the first electrode 210 and the second electrode 220 which are connected to the power source unit 100 and form an open loop circuit therewith. When a part of a user's body comes into contact with the first electrode 210 and the second electrode 220, the power source unit 100, the first electrode 210, and the second electrode 220 form a closed loop circuit. The control unit 500 instructs at least one unit included in the wearable terminal 10 to perform a preset operation by sensing that the closed loop circuit is formed.

For example, when the part of the user's body comes into contact with the first electrode 210 and the second electrode 220, the control unit 500 changes the wearable terminal 10 from the sleep mode to the awake mode. When the part of the user's body comes into contact with the first electrode 210 and the second electrode 220, the control unit 500 may change an operating frequency of the sensor unit 600.

The control unit 500 may change the wearable terminal 10 to perform another function while performing one of the plurality of functions in the awake mode. When the part of the user's body comes into contact with the first electrode 210 and the second electrode 220, or a physical impact is applied to the wearable terminal 10 in response to the contact of the user's body, the control unit 500 may change the wearable terminal 10 from a first mode of performing one function to a second mode of performing another function. The physical impact applied to the wearable terminal 10 is sensed by the sensor of the sensor unit 600. For example, the control unit 500 may sense whether there is a contact of the user's body by calculating an impulse applied to the wearable terminal 10 based on sensing data output from an acceleration sensor.

Figure 7A:
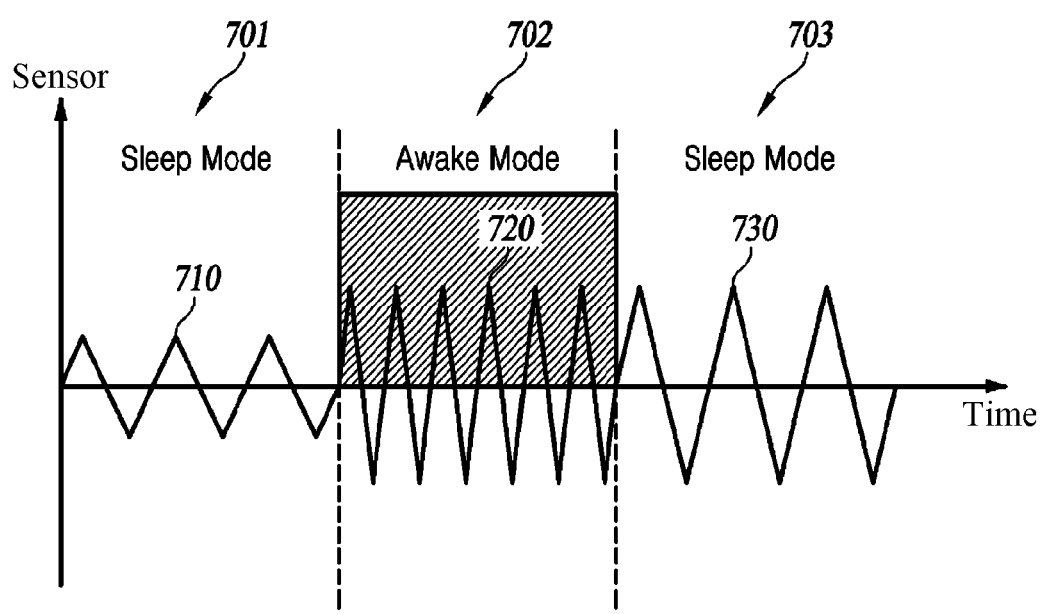
FIG. 7A is a graph illustrating values measured by a sensor of a wearable terminal according to an embodiment of the present invention.

FIG. 7A is a graph illustrating values measured by a sensor of a wearable terminal according to an embodiment of the present invention.

Based on a duration during which a state in which a closed loop circuit is formed is continued in an awake mode 702, it is possible to switch from the awake mode 702 to a sleep mode 703. It may also be possible to switch from the awake mode 702 to the sleep mode 703 based on a time during which a contact of a user is not detected in the awake mode 702.

The sensor unit 600 includes a plurality of sensors that may measure a motion of the user or a physiological condition of the user. A portion of the sensors of the sensor unit 600 senses a physical contact or senses whether a closed loop circuit is formed based on a first frequency preset in the sleep mode. When the wearable terminal 10 is in an awake mode, a portion of the sensors of the sensor unit 600 senses a physical contact or whether a closed loop circuit is formed based on a second frequency which is higher than the first frequency to detect a motion of controlling the device by the user (hereinafter, a contact gesture). Here, the sensor unit 600 may be at least one of a touch sensor mounted on the outer portion of the wearable terminal 10, an acceleration sensor for measuring an acceleration of an object or an impulse, or an EMG sensor for measuring a degree of muscle contraction or relaxation, but is not limited thereto.

Referring to FIG. 7A, operating intervals of a sensor with reference numerals 710 and 730 differ from an operating interval of the sensor with a reference numeral 720. That is, an operating frequency of the sensor in a sleep mode differs from an operating frequency of the sensor in an awake mode. In this example, the operating frequency (second frequency) of the sensor in the awake mode is set to be higher than the operating frequency (first frequency) of the sensor in the sleep mode. Since the device is not controlled by the user in the sleep mode, a level of sensing a contact gesture of the user is lowered at the first frequency. Since the device may be controlled by the user in the awake mode, the level of sensing a contact gesture of the user is increased further at the second frequency.

The sensor of the sensor unit 600 continuously measures the motion or the physiological condition of the user even in the sleep mode, and the sensor unit 600 detects a contact gesture of the user at the same time measuring the motion or the physiological condition of the user in the awake mode. Referring to FIG. 7A, values measured by the sensor with the reference numerals 720 and 730 are greater than a value measured by the sensor with the reference numeral 710. The sensor values measured at the first frequency in the sleep mode are used to verify the motion or the physiological condition of the user, and are not used to detect the contact gesture of the user. That is, in the sleep mode, detection of a contact gesture of the user using the sensor is not performed.

By the wearable terminal according to embodiments, there is no need for installing a separate input device of a user on an outer portion of a main body, and thus a bilaterally symmetric design, a reduction in manufacturing cost, advantageous waterproofing treatment, and removal of main causes of product malfunction may be enabled. Further, the power of the power source unit 100 may be efficiently managed while an operation of the device unrelated to an intention of the user may be prevented.

The contact gesture of the user is at least one of a push, a tap, a slide, a touch, a turn, and a flick. The control unit 500 detects the contact gesture of the user by sensing a physical contact or whether a closed loop circuit is formed, in the awake mode 702. For example, a tap of the user may be detected using an acceleration sensor. However, the contact gesture of the user is not limited thereto, and various motions may be detected.

The wearable terminal 10 may change between a plurality of functions performable in the awake mode based on the contact gesture of the user. That is, the control unit 500 may change a function to be performed by the wearable terminal 10 based on the contact gesture of the user, and change information to be displayed on the display unit 700.

The wearable terminal performing the plurality of functions includes the power source unit 100, the electrode unit 200, the control unit 500, the sensor unit 600, and the display unit 700. The plurality of functions includes a function of changing a function to be performed by the terminal, a function of displaying a clock, a function of analyzing a body composition, a function of displaying a heart rate, a function of displaying a step count, a function of displaying a walking time, a function of displaying a calorie consumption, a function of displaying a traveled distance, a function of displaying a battery level, and a function of transmitting beacon information. The body composition is analyzed by measuring a bioimpedance using the electrode unit 200. The step count is measured using the sensor unit 600.

The electrode unit 200 includes a first electrode and a second electrode. When a part of the user's body comes into contact with the first electrode and the second electrode, the control unit 500 switches the wearable terminal from the sleep mode to the awake mode. The display unit 700 is connected to the control unit 500 and displays information related to at least one of the plurality of functions in the awake mode. The sensor unit 600 is connected to the control unit 500, and senses a physical contact or whether a closed loop circuit is formed. The control unit 500 detects a contact gesture of the user using the sensor unit 600. When a contact gesture of the user is detected, the control unit 500 changes a function to be performed by the wearable terminal 10, and the display unit 700 changes information related to one function to information related to another function, and displays the information related to the other function.

The wearable terminal includes the storing unit 800. The storing unit 800 stores a sequence related to at least two of the function of displaying a clock, the function of analyzing a body composition, the function of displaying a heart rate, the function of displaying a step count, the function of displaying a walking time, the function of displaying a calorie consumption, the function of displaying a traveled distance, and the function of displaying a battery level. When a contact gesture of the user is detected, the display unit 700 displays information related to the at least two functions in sequence. The sequence related to the at least two functions may also be set using an application on a paired mobile device.

Figure 7B:
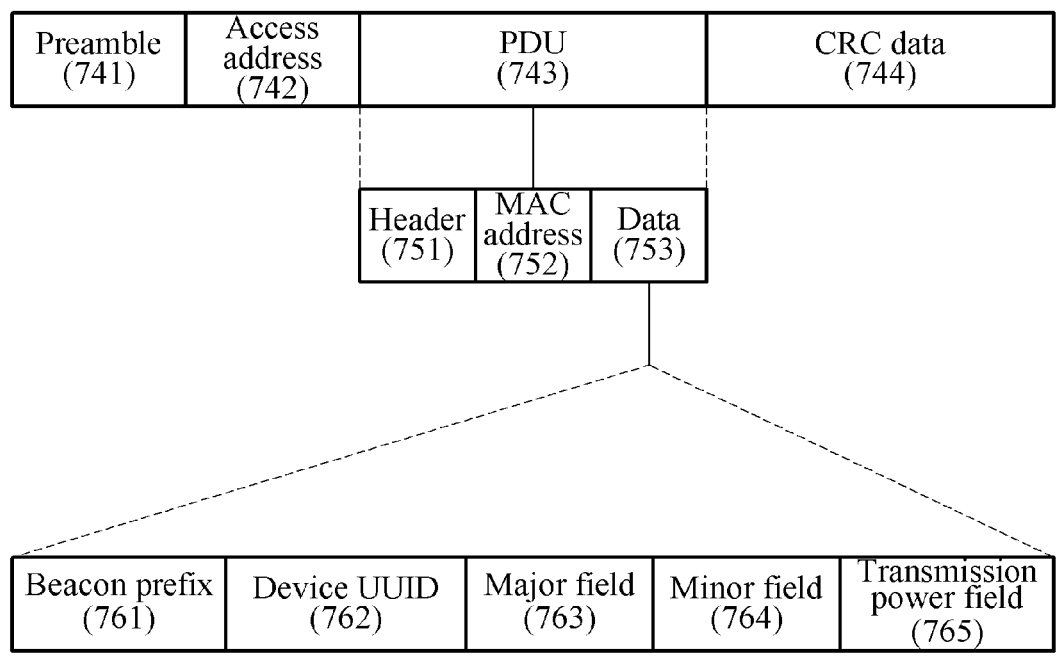
FIG. 7B illustrates a frame structure of beacon information transmitted by a wearable terminal according to an embodiment of the present invention.

FIG. 7B illustrates a frame structure of beacon information transmitted by a wearable terminal according to an embodiment of the present invention. Referring to FIG. 7B, a frame structure of beacon information transmitted by a wearable terminal in the awake mode 702 is illustrated. In detail, the wearable terminal may transmit the beacon information to a designated external device in the awake mode 702. For example, the designated external device may be a device which has a communication interface and performs a predetermined function, such as a security device disposed at a gate of an apartment, a gate device at a library or a gym, or an elevator control device disposed in a building. The designated external device described above is only an exemplary description for helping with understanding of the invention, and is not intended to limit or restrict other embodiments. In detail, an example of implementing the designated external device as a device such as a point of sale (POS) terminal disposed at a supermarket or a smart speaker disposed in a house is also included in the scope of the present embodiment.

The beacon information may include a preamble 741, an access address 742, a protocol data unit (PDU) 743, and cyclical redundancy check (CRC) data 744. The preamble 741 may include control information to determine an access protocol such that the wearable terminal may perform data communication with the designated external device. Further, the preamble 741 may include control information to determine resource information to be used by the wearable terminal for the data communication. The access address 742 may include Internet Protocol address information related to the designated external device. The CRC data 744 may include designated data of a pre-agreed length to detect a data error during a communication process.

Further, the PDU 743 may include a header 751, a MAC address 752, and data 753. The field of the data 753 may include a beacon prefix 761, a device universally unique identifier (UUID) 762, a major field 763, a minor field 764, and a transmission power field 765. The beacon prefix 761 may include data information which summaries an information type of data to be transmitted. The device UUID may be a unique device serial number of a single wearable terminal, and include information to be used by an external device to identify the wearable terminal. Further, the wearable terminal may implement various functions to be performed in the awake mode 702 using values of data bytes assigned to the major field 763 and the minor field 764. Further, the header 751 and the MAC address 752 are obvious to those skilled in the field of Bluetooth-based communication, and thus the detailed description thereof will be omitted.

When the awake mode 702 is entered in response to a contact of the user, the wearable terminal may perform a function of controlling an access (check-in, check-out) to a library, and a function of automatically purchasing a designated product through communication with the designated external device. For example, there may be an example in which a 2-byte data space is assigned to each of the major field 763 and the minor field 764. In this example, the wearable terminal may perform operations as shown in the following Table 1 based on values of the major field 763 and values of the minor field 764, in response to the designated external device.

TABLE 1

| Value of major field 763 | Value of minor field 764 | Function of wearable terminal |
|---|---|---|
| 01 | 01 | Library check-in |
| 01 | 02 | Library check-out |
| 02 | 01 | Purchase first product |
| 02 | 02 | Purchase second product |

The wearable terminal may provide an effect of performing various additional functions by transmitting predetermined beacon information to the designated external device in the awake mode 702. The description provided in Table 1 is only an exemplary description for helping with understanding of the invention, and should not be construed as limiting or restricting other embodiments. For example, the wearable terminal may perform varied functions such as transmitting control information to make an elevator to automatically come down without directly pushing a button of the elevator at a lobby, or transmitting an access request with respect to a parking lot gate of an apartment, by transmitting beacon information in the awake mode 702. Further, the byte size of the data assigned to the major field 763 and the minor field 764 may also be varied depending on an implementation scheme of those skilled in the art.

Figure 8A:
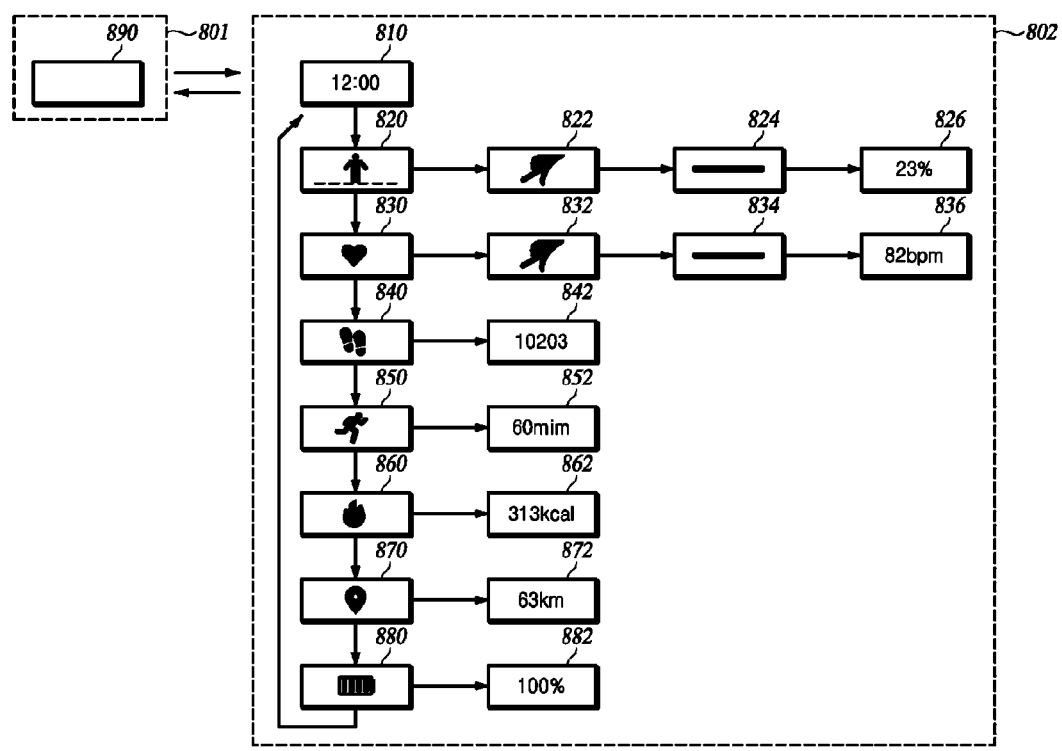
FIG. 8A is a diagram illustrating information displayed by a display unit 700 of a wearable terminal according to an embodiment of the present invention.

FIG. 8A is a diagram illustrating information displayed by a display unit 700 of a wearable terminal according to an embodiment of the present invention.

Referring to FIG. 8A, in a sleep mode 801, the display unit 700 is turned off, as shown in 890. In an awake mode 802, the display unit 700 displays a screen showing information or a function to be provided by a device. The screen displayed by the display unit 700 may include a clock screen 810, body composition measurement screens 820, 822, 824, and 826, heart rate measurement screens 830, 832, 834, and 836, step count screens 840 and 842, walking time screens 850 and 852, calorie consumption screens 860 and 862, traveled distance screens 870 and 872, and battery level screens 880 and 882. The control unit 500 of the wearable terminal 10 may control the display unit 700 to display a screen, and the control unit 500 may control an operation of the display unit 700 in response to a contact gesture of a user.

The body composition measurement screens 820, 822, 824, and 826 may include a screen 820 which shows that a body composition measurement mode is entered, a screen 822 which induces the user to contact electrodes with a finger for body composition measurement, a screen 824 which shows a measurement progress, and a screen 826 which shows a measurement result, and are sequentially displayed on the display unit 700 as the body composition measurement is progressing.

The heart rate measurement screens 830, 832, 834, and 836 may include a screen 830 which shows that a heart rate measurement mode is entered, a screen 832 which induces the user to contact electrodes with a finger for heart rate measurement, a screen 834 which shows a measurement progress, and a screen 826 which shows a measurement result, and are sequentially displayed on the display unit 700 as the heart rate measurement is progressing.

The step count screens 840 and 842 may include a screen 840 which shows that a step count is to be displayed, and a screen 842 which shows a step count. The displayed step count may be a step count measured from a point in time at which a contact gesture of the user is detected, or a step count accumulated from a predetermined point in time. Whether to measure a step count, a measurement start time, and a measurement end time may be set using an application on a paired mobile device.

The walking time screens 850 and 852 may include a screen 850 which shows that a walking time is to be displayed, and a screen 852 which shows a walking time. The displayed walking time is a walking time measured from a point in time at which a contact gesture of the user is detected, or a walking time accumulated from a predetermined point in time. Whether to measure a walking time, a measurement start time, and a measurement end time may be set using an application on a paired mobile device.

The calorie consumption screens 860 and 862 may include a screen 860 which shows that a calorie consumption is to be displayed, and a screen 862 which shows a calorie consumption. The displayed calorie consumption may be a calorie consumption calculated from a point in time at which a contact gesture of the user is detected, or a calorie consumption accumulated from a predetermined point in time. Whether to measure a calorie consumption, a measurement start time, and a measurement end time may be set using an application on a paired mobile device.

The traveled distance screens 870 and 872 may include a screen 870 which shows that a traveled distance is to be displayed, and a screen 872 which shows a traveled distance. The displayed traveled distance may be a traveled distance calculated from a point in time at which a contact gesture of the user is detected, or a traveled distance accumulated from a predetermined point in time. Whether to measure a traveled distance, a measurement start time, and a measurement end time may be set using an application on a paired mobile device.

The battery level screens 880 and 882 may include a screen 880 which shows that a battery level is to be displayed, and a screen 882 which shows a battery level. The battery level may be displayed as a percentage (%) based on an amount of power of the power source unit 100.

Figure 8B:
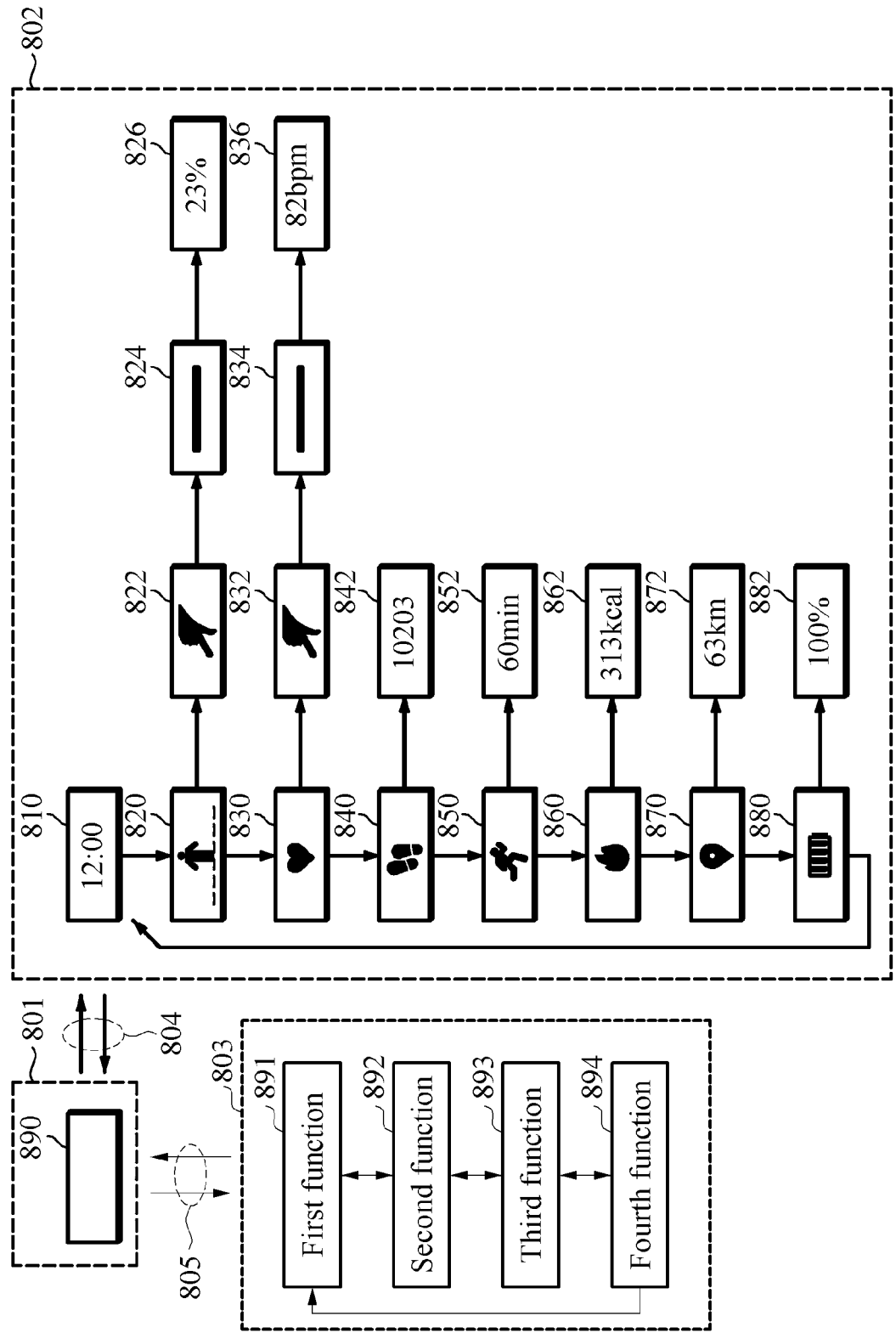
FIG. 8B is a diagram illustrating information displayed by a display unit 700 of a wearable terminal according to another embodiment of the present invention.

FIG. 8B is a diagram illustrating information displayed by a display unit 700 of a wearable terminal according to another embodiment of the present invention.

Referring to FIG. 8B, in the sleep mode 801, the display unit 700 is turned off, as shown in 890. In this example, the wearable terminal may enter one of a first awake mode 802 and a second awake mode 803 in response to a first interaction 804 or a second interaction 805 with a user. For example, the first interaction 804 may be a motion of contacting two electrodes included in the wearable terminal with a part of the user's body. In detail, the first interaction 804 may be a motion of the detection circuit 300 forming a closed loop circuit by connecting a finger of the user to the first electrode 210 and the second electrode 220 of the wearable terminal. Further, the second interaction 805 may be a motion of the user tapping the display unit 700 included in the wearable terminal.

The description of the clock screen 810, the body composition measurement screens 820, 822, 824, and 826, the heart rate measurement screens 830, 832, 834, and 836, the step count screens 840 and 842, the walking time screens 850 and 852, the calorie consumption screens 860 and 862, the traveled distance screens 870 and 872, and the battery level screens 880 and 882 provided with reference to FIG. 8A may apply to screens to be provided in the first awake mode 802, and thus duplicated description will be omitted.

In the second awake mode 802, the wearable terminal may output a plurality of function screens 891, 892, 893, and 894 predetermined by the user. For example, in the second awake mode 802, the wearable terminal may perform a communication mode to transmit beacon information to a designated external device. Further, each of the function screens 891, 892, 893, and 894 may indicate a predetermined function implemented through data communication with the external device.

The user may perform a forward touch or a backward touch by touching one of two electrodes included in the wearable terminal. In response to the forward touch and the backward touch of the user, the wearable terminal may move a function screen to be output for a user by one index (up, down). In detail, the wearable terminal may sequentially output the first function screen 891 through the fourth function screen 894 (891→892→893→894), and also output the first function screen 891 again from the second function screen 892. For example, when the first electrode disposed on an upper side is touched by the user, the wearable terminal may increase an index of a function screen one step in response to the forward touch. Further, when the second electrode disposed on a lower side is touched by the user, the wearable terminal may decrease an index of a function screen one step in response to the backward touch.

The function screens 891, 892, 893, and 894 may respectively correspond to functions of the wearable terminal which are pre-configured by the user. For example, the first function screen 891 may display a function of automatically ordering salads for breakfast of the user, the second function screen 892 may display a function of checking in at a gate of a library, the third function screen 893 may display a function of checking output at the gate of the library, and the fourth screen 894 may display a function of requesting an elevator to automatically move to the first floor at a lobby (first floor) of an apat intent. The plurality of function screens 891, 892, 893, and 894 described above may be implemented through transmission of beacon information. The description provided with reference to FIG. 7B may apply to a frame structure of the transmitted beacon information, and thus duplicated description will be omitted.

Further, the description of the functions described above is only an exemplary description for helping with understanding, and should not be construed as limiting or restricting other embodiments. For example, the user may perform varied functions such as automatically purchasing a designated product, or playing music suitable for the weather/temperature, using a beacon information transmission function of the wearable terminal. Thus, the user may automatically perform data communication with a designated external device using the beacon information transmission function provided by the wearable terminal, whereby an effect of automatically performing an operation such as a purchase, a reservation, an order, or an access within a life radius may be expected.

When the wearable terminal 10 detects a contact gesture of the user, the display unit 700 displays the screens. When the contact gesture of the user is repeated in a predetermined time, that is, when a device detects the contact gesture of the user repeated in a predetermined time (hereinafter, a function switching motion), the display unit 700 sequentially displays the screens each time the contact gesture is detected. In this example, the contact gesture may be one tap. However, the embodiments are not limited thereto.

For example, when the function switching motion is detected while the display unit 700 is displaying the clock 810, that is, when the user inputs a tap into the device, the display unit 700 sequentially switches among a body composition measurement screen, a heart rate measurement screen, and a step count screen and displays a corresponding screen each time the tap is detected.

If a plurality of screens displays information of functions to be provided by the device, only first screens of the screens displaying the corresponding information are displayed in sequence, in response to a detection of the function switching motion. When a contact gesture of the user is not detected any further in a predetermined time, subsequent screens of the screens displaying the corresponding information are displayed. That is, the user may view the first screens displayed in sequence, and select a screen displaying desired information by repeating the contact gesture until the desired information is displayed.

For example, when a repeated contact gesture is not detected any further for a predetermined time while the screen 840 which shows that a step count is to be displayed is displayed, in the middle of sequentially switching a screen displayed on the display unit 700 in response to a detection of a function switching motion, it may be determined that the user selects the function of displaying a step count, and the display unit 700 may display the screen 842 which shows a step count.

The displayed screens and the order of switching the screens shown in FIGS. 8A and 8B are exemplary, and the embodiments are not limited thereto.

The contact gesture of the user may be at least one of a push, a tap, a slide, a touch, a turn, and a flick. The control unit 500 may detect the contact gesture of the user using a sensor which senses a physical contact or whether a closed loop circuit is formed in the awake mode 802.

The contact gesture of the user may be detected based on a contact between the wearable terminal 10 and a part of the user's body or a contact between the wearable terminal 10 and an object. The contact gesture of the user may be detected using an impulse at a time of contact, a contact count, a contact time, a time interval between contacts, a contact region, or a combination thereof.

For example, the contact between the wearable terminal and the part of the user's body may be detected by sensing whether a closed loop circuit flowing in a closed loop circuit including a detection circuit included in the device, two electrodes connected to the detection circuit, and the user's body in contact with the two electrodes is formed. Further, the tap, the push, and the turn of the user may be detected using an acceleration sensor or a touch screen.

The contact gesture of the user may be detected based on a degree of contraction or relaxation of muscle of the contacted part of the user's body. The contact gesture of the user may be detected using a contraction or relaxation count, a contraction or relaxation time, a time interval between contractions or relaxations, a change rate of contraction or relaxation, and a combination thereof. For example, the degree of muscle contraction or relaxation may be detected using an EMG sensor.

By the wearable terminal according to embodiments, there is no need for installing a separate input device of a user on an outer portion of a main body, and it is possible to switch between information displayed on the device or a number of functions provided by the device only through an intuitive motion of the user.

The wearable terminal performing the plurality of functions includes the power source unit 100, the electrode unit 200, the detection circuit 300, the biosignal measurement circuit 400, the control unit 500, the sensor unit 600, the display unit 700, and the storing unit 800. The plurality of functions includes a function of changing a function to be performed by the terminal, a function of displaying a clock, a function of analyzing a body composition, a function of displaying a heart rate, a function of displaying a step count, a function of displaying a walking time, a function of displaying a calorie consumption, a function of displaying a traveled distance, and a function of displaying a battery level. The body composition is analyzed by measuring a bioimpedance using the plurality of electrodes of the electrode unit 200. The step count is measured using a sensor of the sensor unit 600.

Figure 9:
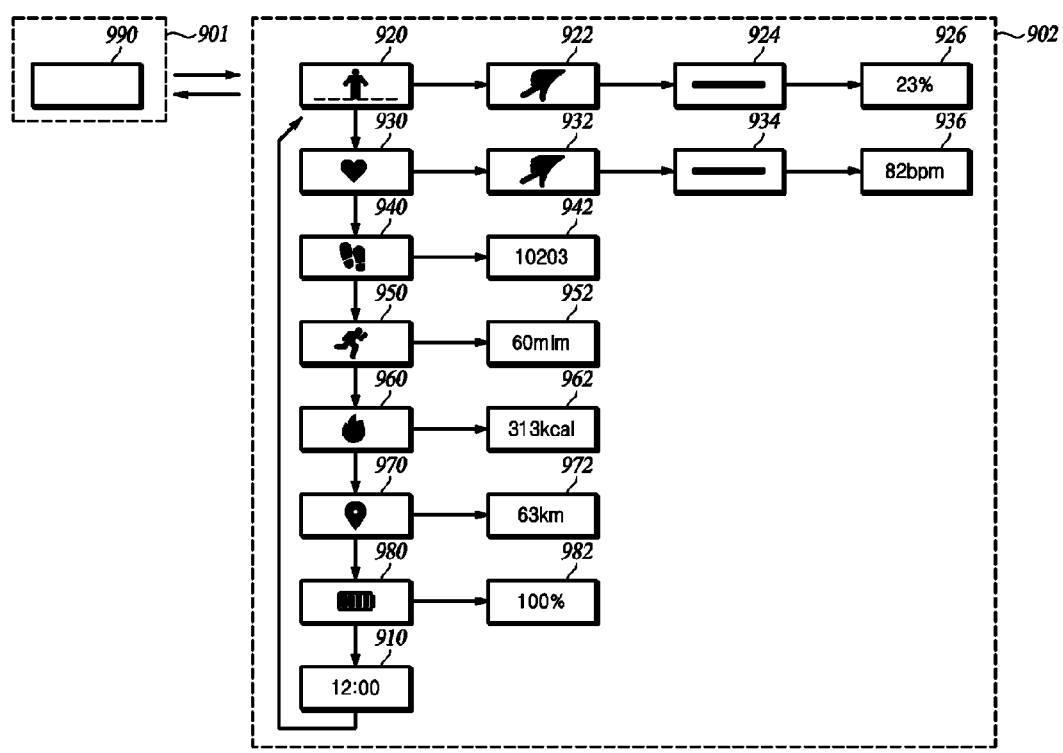
FIG. 9 is a diagram illustrating information displayed by a display unit of a wearable terminal according to still another embodiment of the present invention.

FIG. 9 is a diagram illustrating information displayed by a display unit of a wearable terminal according to still another embodiment of the present invention.

The electrode unit 200 includes the first electrode 210 and the second electrode 220. When a part of a user's body comes into contact with the first electrode 210 and the second electrode 220, the control unit 500 switches the wearable terminal from a sleep mode to an awake mode. The display unit 700 displays information related to at least one of a plurality of functions in the awake mode. The sensor unit 600 senses a physical contact or whether a closed loop circuit is formed. The storing unit 800 stores a plurality of preset contact gestures of a user by matching the plurality of contact gestures to the plurality of functions. The control unit 500 detects one of the plurality of preset contact gestures of the user based on the physical contact of the user sensed by the sensor unit 600. The control unit 500 reads a function corresponding to the detected contact gesture from the storing unit 800. The display unit 700 displays information related to a single function corresponding to a single contact gesture.

The storing unit 800 of the wearable terminal 10 stores the plurality of contact gestures corresponding to the plurality of functions. When a contact gesture of the user is detected, the control unit 500 reads a corresponding function from the storing unit 800, controls the wearable terminal 10 to perform the function corresponding to the contact gesture, and controls the display unit 700 to output a related screen.

Referring to FIG. 9, the display unit 700 displays a clock screen 910, body composition measurement screens 920, 922, 924, and 926, heart rate measurement screens 930, 932, 934, and 936, step count screens 940 and 942, walking time screens 950 and 952, calorie consumption screens 960 and 962, traveled distance screens 970 and 972, and battery level screens 980 and 982 in an awake mode 902. When a contact gesture of the user is detected, the display unit 700 displays a screen related to a function corresponding to the single contact gesture.

The contact gesture of the user is at least one of a push, a tap, a slide, a touch, a turn, and a flick. The control unit 500 may detect the contact gesture of the user using a sensor which senses a physical contact or whether a closed loop circuit is formed in the awake mode 902. For example, a tap of the user may be detected using an acceleration sensor. However, the contact gesture of the user is not limited thereto, and various motions may be detected.

The contact gesture of the user may be detected based on a contact between the wearable terminal 10 and a part of the user's body or a contact between the wearable terminal 10 and an object. The contact gesture of the user may be detected using an impulse at a time of contact, a contact count, a contact time, a time interval between contacts, a contact region, or a combination thereof. For example, such a contact may be detected using the acceleration sensor.

The contact gesture of the user may be detected based on a degree of contraction or relaxation of muscle of the contacted part of the user's body. The contact gesture of the user may be detected using a contraction or relaxation count, a contraction or relaxation time, a time interval between contractions or relaxations, a change rate of contraction or relaxation, and a combination thereof. For example, the degree of muscle contraction or relaxation may be detected using an EMG sensor.

For example, a body composition measurement function corresponds to a tap, and a clock displaying function corresponds to a push. When a tap of the user is detected, the control unit 500 controls the wearable terminal 10 to enter a body composition measurement mode, and controls the display unit 700 to display the body composition measurement screen 920. The display unit 700 sequentially displays the screen 920 which shows the body composition measurement mode is entered, the screen 922 which induces the user to contact electrodes with a finger for body composition measurement, the screen 924 which shows a measurement progress, and the screen 926 which shows a measurement result as the body composition measurement is progressing.

Further, the body composition measurement function corresponds to one tap, and the clock displaying function corresponds to two taps. Such functions performable by the wearable terminal 10 may be matched to various contact gestures.

Such a contact gesture may be detected using sensing data output from the sensor or a temporal pattern in which a closed loop circuit is formed. The temporal pattern in which the closed loop circuit is formed is a pattern in which a part of the user's body comes into contact with the first electrode 210 and the second electrode 220 of the wearable terminal 10. The contact gesture is detected using a contact count between the body and the electrodes, a contact time, and a contact time interval.

For example, when the user successively contacts the first electrode 210 and the second electrode 220 with fingers two times in a predetermined time, a process of forming a closed loop circuit is repeated two times, which corresponds to two taps. The control unit detects the two taps and controls the wearable terminal to perform a function matched to the contact gesture.

A function performed in response to such a contact gesture is not limited by the screen displaying order of the display unit 700 as described with reference to FIGS. 8A and 8B, and a screen to be displayed may be determined based on a contact gesture of the user. That is, when a repeated contact gesture of the user is detected in a predetermined time, a screen to be displayed on the display unit 700 may be switched in sequence. When a contact gesture of the user corresponding to a predetermined function is detected, a function corresponding to the contact gesture is performed, and a related screen is displayed on the display unit 700.

By the wearable terminal according to embodiments, there is no need for installing a separate input device of a user on an outer portion of a main body, and the user may select information to be displayed on the device or a number of functions provided by the device only through a simple motion.

Figure 10:
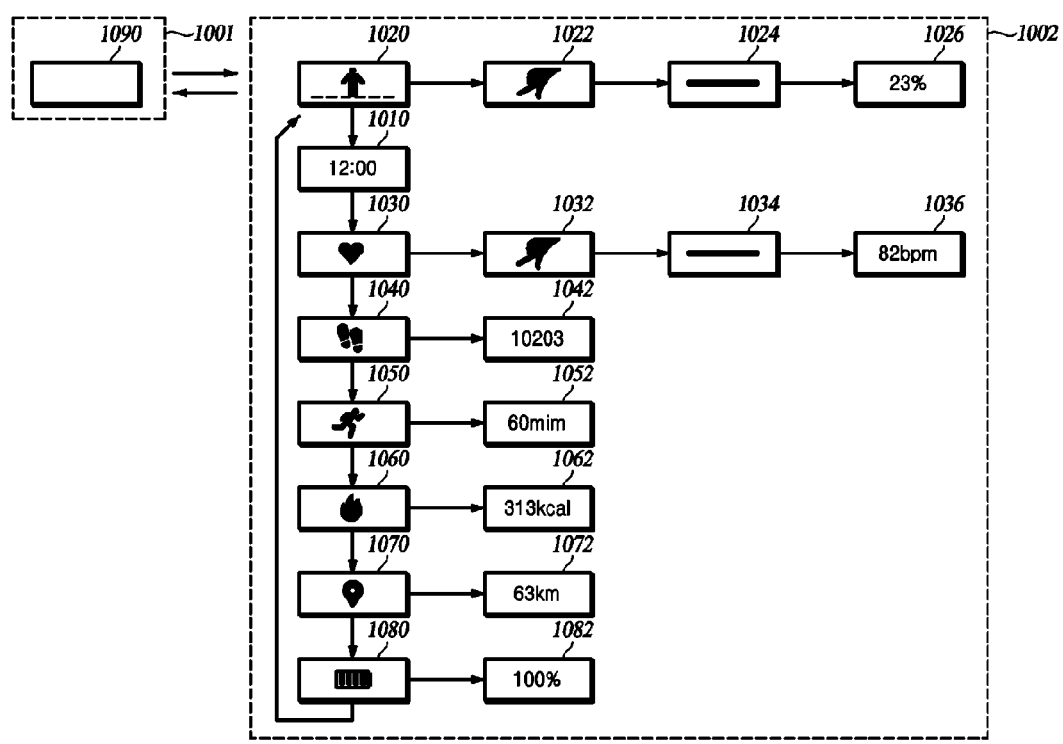
FIG. 10 is a diagram illustrating information displayed by a display unit of a wearable terminal according to yet another embodiment of the present invention.

FIG. 10 is a diagram illustrating information displayed by a display unit of a wearable terminal according to yet another embodiment of the present invention.

The storing unit 800 of the wearable terminal 10 stores frequencies of a plurality of functions performable by a device. When a function switching motion of a user is detected, the control unit 500 compares the frequencies with respect to the plurality of functions stored in the storing unit 800, switches a function to be performed by the wearable terminal 10 in a descending order of the frequencies, and controls the display unit 700 to output a related screen.

Referring to FIG. 10, the display unit 700 displays a clock screen 1010, body composition measurement screens 1020, 1022, 1024, and 1026, heart rate measurement screens 1030, 1032, 1034, and 1036, step count screens 1040 and 1042, walking time screens 1050 and 1052, calorie consumption screens 1060 and 1062, traveled distance screens 1070 and 1072, and battery level screens 1080 and 1082 in an awake mode 1002. When a function switching motion of the user is detected, the display unit 700 sequentially displays the screens. An order of displaying the screens to be switched is determined based on frequencies of functions stored in the storing unit 800.

The frequencies stored in the storing unit 800 are updated each time the user selects a function to be performed by the wearable terminal 10. Either when the user performs a predetermined function through a function switching motion or when the user performs the predetermined function through a contact gesture, the frequencies are updated.

For example, if frequencies of functions decreases in an order of a body composition measurement function, a clock displaying function, a heart rate measurement function, a step count displaying function, a walking time displaying function, a calorie consumption displaying function, a traveled distance displaying function, and a battery level displaying function, a function to be performed by the device is switched in an order of the body composition measurement function, the clock displaying function, the heart rate measurement function, the step count displaying function, the walking time displaying function, the calorie consumption displaying function, the traveled distance displaying function, and the battery level displaying function when a function switching motion of the user is detected.

According to the embodiments described above, a device may perform a function of the device by sensing a contact of a part of a user's body with a first electrode and a second electrode, whereby the electrodes used for body composition analysis may be utilized as an input interface of the user. Thus, it is possible to use electrodes for biosignal measurement as a switch while suppressing inclusion of a separate button-type/touch-type switch.

According to some embodiments, there is no need for installing a separate user input device on an outer portion of a main body, and thus a bilaterally symmetric design which promotes the user convenience, a reduction in manufacturing cost, advantageous waterproofing treatment, and removal of main causes of product malfunction may be enabled, and an operation of a device unrelated to an intention of a user may be prevented. For example, it is also possible to prevent power from being used when a product placed in a box is shaken and waken up from a sleep mode.

Further, although not explicitly mentioned, the effects described herein, which are expected by the technical features of the present invention, and the potential effects thereof may include various effects expected by those skilled in the art based on the description of the present invention.

The processing device described herein may be implemented using hardware components, software components, and/or a combination thereof. For example, the processing device and the component described herein may be implemented using one or more general-purpose or special purpose computers, such as, for example, a processor, a controller and an arithmetic logic unit (ALU), a digital signal processor, a microcomputer, a field programmable gate array (FPGA), a programmable logic unit (PLU), a microprocessor, or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will be appreciated that a processing device may include multiple processing elements and/or multiple types of processing elements. For example, a processing device may include multiple processors or a processor and a controller. In addition, different processing configurations are possible, such as parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The method according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

The invention claimed is:

1. A wearable terminal with a terminal main body and a band connected to the terminal main body so as to be wearable on a body part of a user, the wearable terminal comprising:
    a detection circuit;
    a first electrode and a second electrode which are connected to the detection circuit and spaced apart from each other on a front surface of the wearable terminal;
    a third electrode and a fourth electrode which are connected to the detection circuit and spaced apart from each other on a rear surface of the wearable terminal to contact the body part when the user wears the wearable terminal;
    a control unit for controlling the wearable terminal to perform a pre-configured function when the user's skin contacts the first electrode, the second electrode, the third electrode, and the fourth electrode simultaneously to form a closed loop circuit by the detection circuit, the first electrode, the second electrode, the third electrode, and the fourth electrode through a signal pathway with the user;

a sensor for sensing a contact of the user, wherein the sensor detects the user's contact based on a first frequency in a sleep mode of the wearable terminal and detects the user's contact based on a second frequency higher than the first frequency in an awake mode of the wearable terminal; and a storing unit for storing a plurality of functions, frequencies with which the functions are performed, and a plurality of contact gestures corresponding to the plurality of functions, wherein a plurality of functions include at least two of a function of displaying a clock, the function of analyzing a body composition, the function of displaying a heart rate, the function of displaying a step count, the function of displaying a walking time, the function of displaying a calorie consumption, the function of displaying a traveled distance, and a function of displaying a battery level, wherein a sequence of the plurality of functions is set using at least one application of a paired mobile device, wherein the sequence of the plurality of functions is implemented through the paired mobile device, wherein the sensor includes an acceleration sensor, wherein the control unit senses a contact gesture of the user based on whether the closed loop circuit is formed or sensing data output from the sensor, senses the contact gesture by calculating an impulse applied to the wearable terminal based on sensing data output from the acceleration sensor, and compares the frequencies with respect to the plurality of functions and sets an order of changing the functions to be performed by the wearable terminal, in a descending order of the frequencies;

wherein the control unit detects a contact gesture of the user using sensing data output from the sensor or a temporal pattern in which the signal pathway is formed, determines whether the contact gesture of the user matches one of the plurality of contact gestures stored in the storing unit, reads a function corresponding to the matching contact gesture from the storing unit, and controls the wearable terminal to perform the read function.

2. The wearable terminal of claim 1, wherein when the signal pathway is formed in a sleep mode, the control unit compares a duration of a state in which the signal pathway is formed to a preset threshold, and switches the wearable terminal from the sleep mode to an awake mode when the duration is greater than the preset threshold.

3. The wearable terminal of claim 1, wherein the control unit sequentially changes functions to be performed by the wearable terminal when the contact gesture is sensed in an awake mode.

4. The wearable terminal of claim 1, wherein the control unit detects the contact gesture of the user using an impulse at a time of contact, a contact count, a contact time, a time interval between contacts, a contact region, or a combination thereof, based on the sensing data or the temporal pattern.

5. The wearable terminal of claim 4, wherein the contact gesture includes at least one of a push, a tap, a slide, a touch, a turn, and a flick.

6. The wearable terminal of claim 1, wherein the preconfigured function is sending information including set information.

7. The wearable terminal of claim 6, wherein the sending of the information is beacon transmission.

8. The wearable terminal of claim 1, wherein an operation mode of the wearable terminal is switched from the awake mode to the sleep mode based on a duration of a state in which the closed loop circuit is formed in the awake mode.

9. A wearable terminal with a terminal main body and a band connected to the terminal main body so as to be wearable on a body part of a user, the wearable terminal comprising:

a biosignal measurement circuit;

a first electrode and a second electrode which are connected to the biosignal measurement circuit, and are positioned on a front surface of the wearable terminal to be spaced apart from each other;

a third electrode and a fourth electrode which are connected to the biosignal measurement circuit, and are positioned on a rear surface of the wearable terminal to be spaced apart from each other such that the third electrode and the fourth electrode come into contact with a part of a user's body when the user wears the wearable terminal; and a control unit for sensing a contact of the user's skin with the first electrode through the fourth electrode when another body part of the user that is not wearing the wearable terminal contacts the first electrode and the second electrode, and controlling at least one of the first electrode through the fourth electrode to operate in a biosignal measurement mode when a predetermined time elapses while the user's skin contacts the first electrode, the second electrode, the third electrode, and the fourth electrode simultaneously to form a closed loop circuit by the detection circuit, the first electrode, the second electrode, the third electrode, and the fourth electrode through a signal pathway with the user;

a sensor for sensing a contact of the user, wherein the sensor detects the user's contact based on a first frequency in a sleep mode of the wearable terminal and detects the user's contact based on a second frequency higher than the first frequency in an awake mode of the wearable terminal; and a storing unit for storing a plurality of functions, frequencies with which the functions are performed, and a plurality of contact gestures corresponding to the plurality of functions, wherein a plurality of functions include at least two of a function of displaying a clock, the function of analyzing a body composition, the function of displaying a heart rate, the function of displaying a step count, the function of displaying a walking time, the function of displaying a calorie consumption, the function of displaying a traveled distance, and a function of displaying a battery level, wherein a sequence of the plurality of functions is set using at least one application of a paired mobile device, wherein the sequence of the plurality of functions is implemented through the paired mobile device, wherein the sensor includes an acceleration sensor, wherein the control unit senses a contact gesture of the user based on whether the closed loop circuit is formed or sensing data output from the sensor, senses the contact gesture by calculating an impulse applied to the wearable terminal based on sensing data output from the acceleration sensor, and compares the frequencies with respect to the plurality of functions and sets an order of changing the functions to be performed by the wearable terminal, in a descending order of the frequencies;

wherein the control unit detects a contact gesture of the user using sensing data output from the sensor or a temporal pattern in which the signal pathway is formed, determines whether the contact gesture of the user matches one of the plurality of contact gestures stored in the storing unit, reads a function corresponding to the matching contact gesture from the storing unit, and controls the wearable terminal to perform the read function.

10. The wearable terminal of claim 9, wherein when the wearable terminal operates in the biosignal measurement mode,
the first electrode and the third electrode apply currents to the user's body,
the second electrode and the fourth electrode detect a voltage of a contact site of the body, and
the control unit calculates a bioimpedance of the user based on the detected voltage, and analyzes a body composition of the user based on the bioimpedance.

11. The wearable terminal of claim 9, wherein the control unit determines that the part of the user's body is in contact with the first electrode through the fourth electrode by sensing that the first electrode through the fourth electrode and the biosignal measurement circuit form a closed loop circuit.

12. The wearable terminal of claim 9, wherein the biosignal measurement mode includes at least one of a body composition measurement mode, an electrocardiogram measurement mode, a heart rate measurement mode, a blood flow rate measurement mode, and a blood pressure measurement mode.

13. A wearable terminal for measuring a physiological condition of a user or a motion of the user, the wearable terminal comprising:
a detection circuit,
a first electrode and a second electrode which are connected to the detection circuit and spaced apart from each other on a front surface of the wearable terminal;
a third electrode and a fourth electrode which are connected to the detection circuit and spaced apart from each other on a rear surface of the wearable terminal to contact the body part when the user wears the wearable terminal;
a control unit for controlling the wearable terminal to perform a pre-configured function when the user's skin contacts the first electrode, the second electrode, the third electrode, and the fourth electrode simultaneously to form a closed loop circuit by the detection circuit, the first electrode, the second electrode, the third electrode, and the fourth electrode through a signal pathway with the user;
a sensor for sensing a contact of the user, wherein the sensor detects the user's contact based on a first frequency in a sleep mode of the wearable terminal and detects the user's contact based on a second frequency higher than the first frequency in an awake mode of the wearable terminal; and
a storing unit for storing a plurality of functions, frequencies with which the functions are performed, and a plurality of contact gestures corresponding to the plurality of functions, wherein a plurality of functions include at least two of a function of displaying a clock, the function of analyzing a body composition, the function of displaying a heart rate, the function of displaying a step count, the function of displaying a walking time, the function of displaying a calorie consumption, the function of displaying a traveled distance, and a function of displaying a battery level,
wherein a sequence of the plurality of functions is set using at least one application of a paired mobile device,
wherein the sequence of the plurality of functions is implemented through the paired mobile device,
wherein the sensor includes an acceleration sensor,
wherein the control unit
senses a contact gesture of the user based on whether the closed loop circuit is formed or sensing data output from the sensor,
senses the contact gesture by calculating an impulse applied to the wearable terminal based on sensing data output from the acceleration sensor, and
compares the frequencies with respect to the plurality of functions and sets an order of changing the functions to be performed by the wearable terminal, in a descending order of the frequencies;
wherein the control unit detects a contact gesture of the user using sensing data output from the sensor or a temporal pattern in which the signal pathway is formed, determines whether the contact gesture of the user matches one of the plurality of contact gestures stored in the storing unit, reads a function corresponding to the matching contact gesture from the storing unit, and controls the wearable terminal to perform the read function.

14. The wearable terminal of claim 13, wherein when a predetermined time elapses while the user's body is in contact with the first electrode and the second electrode simultaneously in a sleep mode, the control unit switches the wearable terminal from the sleep mode to an awake mode.

15. The wearable terminal of claim 13, wherein the control unit sequentially changes functions to be performed by the wearable terminal when the contact gesture is sensed in an awake mode.

16. The wearable terminal of claim 15, wherein the control unit senses a contact gesture of the user using a temporal pattern in which the user's body comes into contact with the first electrode and the second electrode or sensing data output from the sensor, reads a function corresponding to the sensed contact gesture from the storing unit, and controls the wearable terminal to perform the read function.

17. The wearable terminal of claim 16, wherein the control unit detects the contact gesture of the user using an impulse at a time of contact, a contact count, a contact time, a time interval between contacts, a contact region, or a combination thereof, based on the sensing data or the temporal pattern.

18. The wearable terminal of claim 17, wherein the contact gesture includes at least one of a push, a tap, a slide, a touch, a turn, and a flick.

* * * * *